(12) United States Patent
Yu

(10) Patent No.: US 11,364,201 B2
(45) Date of Patent: *Jun. 21, 2022

(54) NANO-LIPOSOME CARRIER COMPOSITION CONTAINING HYBRID OF CAS9 PROTEIN AND GUIDE RNA

(71) Applicant: Moogene Medi Co. Ltd., Daejeon (KR)

(72) Inventor: Kyeong-Nam Yu, Suwon-si (KR)

(73) Assignee: Moogene Medi Co., Ltd.

(*) Notice: Subject to any disclaimer, the term of this patent is extended or adjusted under 35 U.S.C. 154(b) by 211 days.

This patent is subject to a terminal disclaimer.

(21) Appl. No.: 16/438,539

(22) Filed: Jun. 12, 2019

(65) Prior Publication Data

US 2020/0146988 A1     May 14, 2020

Related U.S. Application Data

(63) Continuation of application No. 15/837,987, filed on Dec. 11, 2017, now Pat. No. 10,363,217, which is a continuation of application No. PCT/KR2017/003805, filed on Apr. 7, 2017.

(30) Foreign Application Priority Data

Aug. 10, 2016 (KR) .................. 10-2016-0101701

(51) Int. Cl.

| | |
|---|---|
| A61K 9/127 | (2006.01) |
| A61K 47/69 | (2017.01) |
| A61K 48/00 | (2006.01) |
| A61P 3/10 | (2006.01) |
| C12N 15/11 | (2006.01) |
| C12N 15/113 | (2010.01) |
| C12N 15/88 | (2006.01) |
| C12N 15/90 | (2006.01) |
| C12N 9/22 | (2006.01) |

(52) U.S. Cl.
CPC .......... *A61K 9/1272* (2013.01); *A61K 9/127* (2013.01); *A61K 47/6911* (2017.08); *A61K 48/00* (2013.01); *A61K 48/0041* (2013.01); *A61P 3/10* (2018.01); *C12N 9/22* (2013.01); *C12N 15/11* (2013.01); *C12N 15/1137* (2013.01); *C12N 15/88* (2013.01); *C12N 15/90* (2013.01); *C12N 2310/20* (2017.05); *C12N 2320/32* (2013.01)

(58) Field of Classification Search
None
See application file for complete search history.

(56) References Cited

U.S. PATENT DOCUMENTS

| | | |
|---|---|---|
| 7,341,835 B2 | 3/2008 | Blume |
| 8,697,359 B1 | 4/2014 | Zhang |
| 10,363,217 B2 * | 7/2019 | Yu ............... C12N 15/1137 |
| 2015/0071903 A1 | 3/2015 | Liu |
| 2015/0118216 A1 | 4/2015 | Liu |
| 2015/0232883 A1 | 8/2015 | Dahlman |
| 2015/0344912 A1 | 12/2015 | Kim |
| 2016/0130608 A1 | 5/2016 | Doudna |
| 2016/0237455 A1 | 8/2016 | Glucksmann |
| 2016/0355795 A1 | 12/2016 | Ran |
| 2017/0107539 A1 | 4/2017 | Yu |
| 2017/0166893 A1 | 6/2017 | Doudna |

FOREIGN PATENT DOCUMENTS

| | | |
|---|---|---|
| EP | 3087974 A1 | 11/2016 |
| KR | 10-2015-0101476 A1 | 9/2015 |
| KR | 10-2015-0101477 A1 | 9/2015 |
| KR | 10-2015-0101478 A1 | 9/2015 |
| WO | WO 2014/204728 | 12/2014 |
| WO | WO 2016/057061 A1 | 4/2016 |
| WO | WO 2016/100857 | 6/2016 |
| WO | WO 2016/118697 A1 | 7/2016 |
| WO | WO 2016/123514 A1 | 8/2016 |
| WO | WO 2016/164356 A1 | 10/2016 |
| WO | WO 2016/197133 A1 | 12/2016 |
| WO | WO 2016/205613 A1 | 12/2016 |
| WO | WO 2017/035659 A1 | 3/2017 |
| WO | WO 2017/066707 A1 | 4/2017 |
| WO | WO 2017/083274 A1 | 5/2017 |

OTHER PUBLICATIONS

Lenski M et al., "Effects of DPP-4 inhibition on cardiac metabolism and function in mice." J. Mol. Cell Cardiol., 51(6), 906-918, 2011).
Ramakrishna S. et al., "Gene disruption by cell-penetrating peptide-mediated delivery of Cas9 protein and guide RNA," Genome Res., 24(6), 1020-1027, 2014).
Woo JW et al., "DNA-free genome editing in plants with preassembled CRISPR-Cas9 ribonucleoproteins," Nat. Biotechnol., 33(11), 1162-1164, 2015.
Zuris et al., "Cationic lipid-mediated delivery of proteins enables efficient protein-based genome editing in vitro and in vivo," Nat. Biotechnol., 33(1), 73-80 (2015).
Omar, et al. (Jun. 18, 2014) "Dipeptidyl peptidase 4 (DPP-4) is expressed in mouse and human islets and its activity is decreased in human islets from individuals with type 2 diabetes" Diabetologia, 57: 1876-83.
Zillessen, et al. (Mar. 17, 2016) "Metabolic role of dipeptidyl peptidase 4 (DPP4) in primary human (pre)adipocytes", Scientific Reports, 6: article No. 23074 (pp. 1-12).
GenBank Accession No. S79876.1, "dipeptidyl peptidase IV {promoter} [human, placenta, Genomic, 2435 nt]," Jul. 14, 2016, 2 pages.

(Continued)

*Primary Examiner* — Robert M Kelly
(74) *Attorney, Agent, or Firm* — Fish & Richardson P.C.

(57) ABSTRACT

The present invention relates to nano-liposome carrier compositions that encapsulate a hybrid of a Cas9 protein and a guide RNA and methods of making and using the same. The nano-liposome carrier compositions have an excellent effect of suppressing expression of target DNA, and thus pharmaceutical compositions including the nano-liposome carrier compositions can be used for treating diseases such as diabetes.

22 Claims, 16 Drawing Sheets

Specification includes a Sequence Listing.

(56) References Cited

OTHER PUBLICATIONS

Kee et al., "Synthesis, acoustic stability, and pharmacologic activities of papaverine-loaded echogenic liposomes for ultrasound controlled drug delivery," Journal of Liposome Research, Jan. 1, 2008, 18(4):263-77.
PCT International Search Report and Written Opinion in International Appln. No. PCT/KR2017/003805, dated Jul. 10, 2017, 22 pages (with English translation).
Wang et al., "In vivo delivery systems for therapeutic genome editing," International Journal of Molecular Sciences, May 2016, 17(5):626, 19 pages.

\* cited by examiner

🦠 Lecithin
🫧 Cholesterol
🧬 DOGS-NTA-Ni
🪱 Cas9/guide RNA complex
🌿 PEI
🪱 Cas9/guide RNA complex coated PEI ① Loading Cas9

② NL-Cas9/gDPP4 : Comparative example 3

③ NL(Ni)-Cas9/gDPP4 : Comparative example 4

④ NL(Ni)-Cas9/gDPP4(PEI) : Example 2

NANO-LIPOSOME CARRIER COMPOSITION CONTAINING HYBRID OF CAS9 PROTEIN AND GUIDE RNA

CROSS REFERENCE TO RELATED APPLICATIONS

This application is a continuation of U.S. application Ser. No. 15/837,987, filed Dec. 11, 2017, now U.S. Pat. No. 10,363,217, which is a continuation of International Application PCT/KR2017/003805, filed on Apr. 7, 2017, which claims priority from Korean Patent Application No. KR 10-2016-0101701, filed on Aug. 10, 2016, all of which are incorporated herein by reference in their entireties.

SEQUENCE LISTING

The present application contains a Sequence Listing that has been submitted electronically in ASCII format and is hereby incorporated by reference in its entirety. The ASCII copy, created on Jun. 11, 2019, is named 44987_0002002.txt and is 5,920 bytes in size

TECHNICAL FIELD

The present invention relates to carrier compositions containing a hybrid of a Cas9 protein and a guide RNA. More specifically, the present invention relates to carrier compositions that encapsulate a hybrid of Cas9 protein and a guide RNA that is specific to a target DNA.

BACKGROUND

The technique of genome editing is derived from adaptive immunity of microorganisms. It is based on an immune system which functions by storing a fragment of a bacteriophage DNA when infected and, upon subsequent infections, the stored sequence is cut and removed by Clustered Regularly Interspaced Short Palindromic Repeats (CRISPR)-associated protein 9 (Cas9: RNA-guided DNA endonuclease enzyme), a nuclease serving as genetic scissors. This process has been developed into a gene correction technique capable of cutting and fixing a desired region even in a genome if a specific base sequence can be recognized by a guide RNA (gRNA) (Woo J W et al., "DNA-free genome editing in plants with preassembled CRISPR-Cas9 ribonucleoproteins," Nat. Biotechnol., 33(11), 1162-1164, 2015).

This CRISPR technique has drawn much attention as a method capable of treating fundamental causes of diseases induced due to genetic disorders that previously had been classified as incurable diseases. However, there are still problems to be solved, such as inefficient in vive delivery of a gene editing system and cutting of non-target genes, known as "off-targeting." In particular, the use of a gene editing system using a Cas9 plasmid, which was the earliest CRISPR method, had to be inspected for safety reasons such as antibiotic resistance and various immune reactions during in vive delivery. Recently, an alternate system for producing protein gene scissors (Cas9) and guide RNA in a test tube and delivering the resulting product was utilized, but this system also has problems in terms of efficiency of delivery into cells and safety of the protein and RNA (Ramakrishna S. et al., "Gene disruption by cell-penetrating peptide-mediated delivery of Cas9 protein and guide RNA," Genome Res., 24(6), 1020-1027, 2014).

Additional references are known in this field of gene editing. For example, see, Korean Published Patent No. 10-2015-0101476 ("Target DNA delivery composition including nucleic acid or Cas protein for encoding guide RNA specific to target DNA and Cas protein and use of same, applicant") filed by Toolgene Inc. and published on Sep. 3, 2015;

Korean Published Patent No. 10-2015-0101477 ("Target DNA cutting composition including nucleic acid or Cas protein for encoding guide RNA specific to target DNA and Cas protein and use of same") filed by Toolgene Inc. and published on Sep. 3, 2015; and Korean Published Patent No. 10-2015-0101478 ("Target DNA cutting composition including nucleic acid or Cas protein for encoding guide RNA specific to target DNA and Cas protein and use of same") filed by Toolgene Inc., publication date: Sep. 3, 2015).

Type 2 diabetes is a disease in which normal sugar metabolism is not taking place due to a relative increase in insulin resistance caused by various causes although an insulin secreting function remains. In particular, glucagon-like peptide-1 (GLP-1), which is involved in insulin resistance, regulates insulin secretion in the pancreas. It is known that in type 2 diabetes there is an increased expression of dipeptidyl peptidase-4 (DPP4), which is known to decompose GLP-1, which in turn leads to increased insulin resistance. In practice, sitagliptin, a known DPP4 inhibitor, and the like are used as medicines for treating type 2 diabetes. However, when such DPP4 inhibitors are used in a formulation, the effect is temporary. Thus, these medicines must be taken every day, and the use thereof with respect to type 2 diabetes accompanying kidney disorders is limited because of side effects. In addition, various other side effects including allergic reactions caused by the medicine have been reported (Lenski M et al., "Effects of DPP-4 inhibition on cardiac metabolism and function in mice." J. Mol. Cell Cardiol., 51(6), 906-918, 2011).

SUMMARY

The present inventors have produced nano-liposome carriers having good drug delivery efficiency by encapsulating hybrids of a Cas9 protein and a guide RNA in a nano-liposome including 1,2-dioleoyl-sn-glycero-3-[(N-5-amino-1-carboxypentyl) iminodiacetic acid) succinyl] (nickel salt) (DOGS-NTA-Ni) lipid. With guide RNAs that target the DPP4 gene, these new carriers can be used in methods to treat type 2 diabetes by gene editing.

In one aspect, the present invention relates to nano-liposome carrier compositions containing a hybrid of Cas9 protein and a guide RNA. More specifically, the present invention relates to a nano-liposome carrier composition in which a hybrid of Cas9 protein and a guide RNA, which is specific to target DNA, are encapsulated. The nano-liposome carrier compositions have an excellent effect in suppressing expression of a target DNA, and thus blood sugar can be effectively managed for a long time through a single injection even without daily administration of a diabetes therapeutic agent. Thus, a pharmaceutical composition including the nano-liposome carrier compositions can be conveniently used as a pharmaceutical composition for alleviating or treating diseases such as diabetes.

The compositions can be produced by combining a cationic polymer with the hybrid of a Cas9 protein and a guide RNA that is specific to a target DNA. The cationic polymer can be selected from one or more of poly-L-lysine, polyamidoamine, poly[2-(N,N-dimethylamino)ethyl methacrylate], chitosan, poly-L-ornithine, cyclodextrin, histone, collagen, dextran, and polyethyleneimine.

The nano-liposomes can include lecithin, cholesterol, and a metal chelating lipid and can have a particle size of 10-2,000 nm.

In another aspect, the present invention provides compositions for alleviating or treating type 2 diabetes, wherein the compositions contain the nano-liposome carrier compositions described herein.

With respect to the compositions for alleviating or treating type 2 diabetes, the nano-liposome carrier compositions can contain, as a guide RNA specific to target DNA, a guide RNA for suppressing expression of DPP4. The guide RNA, as a single-stranded guide RNA, can have a base nucleic acid sequence of SEQ ID NO: 1 or 2:

```
                              (SEQ ID NO: 1)
UUUGGGCCAUUUGGGGAGUU
                              (SEQ ID NO: 2)
GUCCGGUUUCGCCAGCUUUU
```

In another aspect, the present invention provides methods for producing the nano-liposome carrier compositions described herein. In some embodiments, the methods can include a first step of producing a hybrid of a Cas9 protein and a guide RNA that is specific to a target DNA, and producing a lipid film composition by mixing lecithin, metal chelating lipid, and cholesterol in a chloroform. In a second step, the hybrid of the Cas9 protein and the guide RNA specific to the target DNA are added to the lipid film composition and the resulting mixture is treated by sonication. In a third step, the sonicated lipid film composition mixture is frozen and thawed one or more times and is re-treated by sonication. In a fourth step, the sonicated lipid film composition is centrifuged, and pelleted materials are collected.

The compositions can be produced by combining a cationic polymer with the hybrid from the first step.

The Cas9 protein and the guide RNA can be mixed at a molar ratio of 1:1-3 when producing the hybrid of the first step. The lecithin, the metal chelating lipid, and the cholesterol of the first step can be mixed at a molar ratio of 1.5-2.5:0.5-1.5:0.1-0.5. Herein, the freezing and thawing of the third step may be performed 3-6 times.

In another aspect, the disclosure relates to compositions including (a) a nano-liposome carrier including lecithin (e.g., α-phosphatidylcholine), cholesterol, and metal chelating lipid; and (b) a hybrid Clustered Regularly Interspaced Short Palindromic Repeats (CRISPR) complex that includes (i) a CRISPR-associated protein 9 (Cas9) protein, (ii) a guide RNA that specifically binds to a target DNA of a human dipeptidyl peptidase-4 (DPP4) gene, and (iii) a cationic polymer; wherein the nano-liposome carrier encapsulates the hybrid CRISPR complex.

In some embodiments, the metal chelating lipid used in these compositions is selected from the group consisting of: 1,2-dioleoyl-sn-glycero-3-[(N-5-amino-1-carboxypentyl)iminodiacetic acid) succinyl] (nickel salt) ("DOGS-NTA-Ni"); 1,2-dimyristoyl-sn-glycero-3-phosphoethanolamine-N-diethylenetriamine-pentaacetic acid (gadolinium salt) ("DMPE-DTPA-Gd"); and 1,2-dimyristoyl-sn-glycero-3-phosphoethanolamine-N-diethylenetriamine-pentaacetic acid (copper salt) ("DMPE-DTPA-Cu"), wherein the DOGS-NTA-Ni lipid has a chemical structure shown in Chemical Formula 1 below, Chemical Formula 1

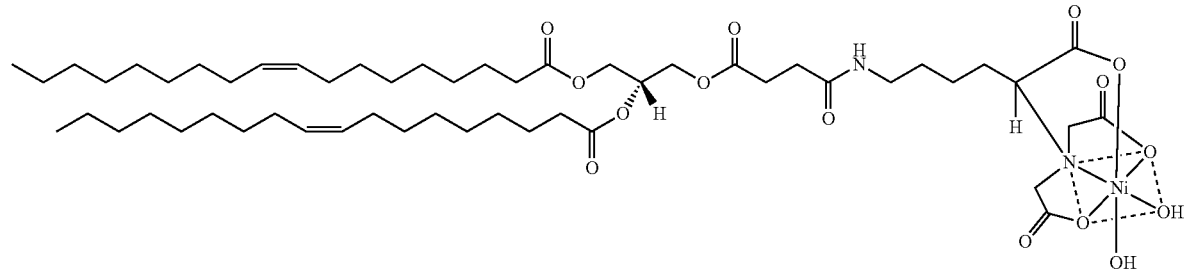

wherein the DMPE-DTPA-Gd lipid has a chemical structure shown in Chemical Formula 2 below, Chemical Formula 2

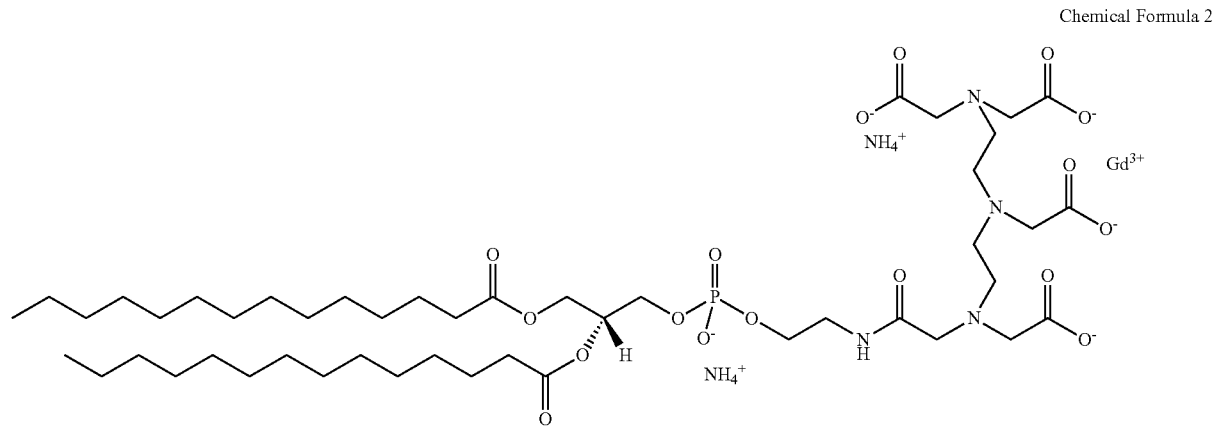

and,
wherein the DMPE-DTPA-Cu lipid has a chemical structure shown in Chemical Formula 3 below, Chemical Formula 3

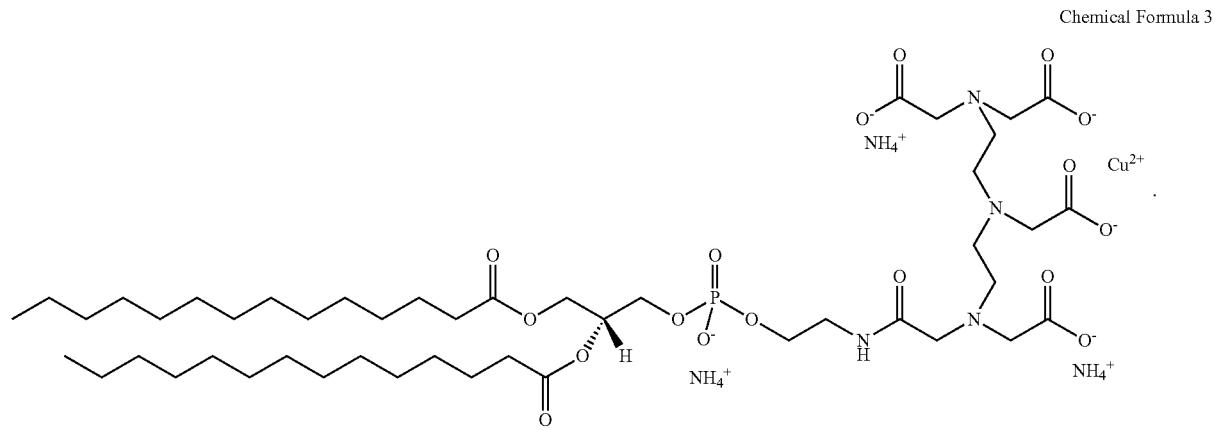

In various embodiments, the cationic polymer is selected from the group consisting of poly-L-lysine, polyamidoamine, poly[2-(N,N-dimethylamino)ethyl methacrylate], chitosan, poly-L-omithine, cyclodextrin, histone, collagen, dextran, and polyethyleneimine (PEI).

In certain embodiments, the guide RNA includes or is the nucleic acid sequence UUUGGGCCAUUUGGGGAGUU (SEQ ID NO: 1) and the target DNA includes or is the nucleic acid sequence AACTCCCCAAATGGCCCAAA (SEQ ID NO:5). In other embodiments, the guide RNA includes or is the nucleic acid sequence GUCCG-GUUUCGCCAGCUUUU (SEQ ID NO:2) and the target DNA includes or is the nucleic acid sequence AAAAGCTGGCGAAACCGGAC (SEQ ID NO:6).

In these compositions, the nano-liposome carrier can have a diameter of 10 to 2,000 nm, e.g., 25 to 1500 nm, 50 to 1000 nm, 75-500 nm, or 100 to 500 nm. In certain embodiments, the Cas9 protein and guide RNA are present in the CRISPR complex at a molar ratio of 1:1-3, e.g., 1:1, 1:2, or 1:3. In some embodiments, the lecithin, metal chelating lipid, and cholesterol are present in the nano-liposome carrier at a molar ratio of 1.5-2.5:0.5-1.5:0.1-0.5, e.g., 1.5:0.1:0.1, or 2.0:1.0:0.25, or 2.5:1.5:0.5.

In certain embodiments, the lecithin is or includes α-phosphatidylcholine, the cationic polymer is or includes polyethyleneimine (PEI), and the metal chelating lipid is DOGS-NTA-Ni. In some embodiments, the Cas9 protein and the guide RNA are present in the CRISPR complex at a molar ratio of 1:1-3 and wherein the lecithin, the metal chelating lipid, and the cholesterol are present in the nano-liposome carrier at a molar ratio of 1.5-2.5:0.5-1.5:0.1-0.5. In certain embodiments, the guide RNA is or includes the nucleic acid sequence UUUGGGCCAUUUGGGGAGUU (SEQ ID NO: 1) or the nucleic acid sequence GUCCG-GUUUCGCCAGCUUUU (SEQ ID NO:2) and the target DNA is or includes the nucleic acid sequence AACTCCC-CAAATGGCCCAAA (SEQ ID NO:5) or the nucleic acid sequence AAAAGCTGGCGAAACCGGAC (SEQ ID NO:6).

In specific embodiments, the Cas9 protein, the guide RNA, and polyethyleneimine are present in the CRISPR complex at a molar ratio of 1:2:50, and the lecithin, DOGS-NTA-Ni lipid, and cholesterol are present in the nano-liposome carrier at a molar ratio of 2:1:0.3.

In another aspect, the disclosure relates to methods for treating a human subject diagnosed with type 2 diabetes, wherein the method includes administering to the subject an amount of a composition effective to reduce expression of the dipeptidyl peptidase-4 (DPP4) gene, wherein the composition includes the compositions described herein, e.g., including (a) a nano-liposome carrier comprising lecithin, cholesterol, and metal chelating lipid; and (b) a hybrid CRISPR complex including (i) a CRISPR-associated protein 9 (Cas9) protein, (ii) a guide RNA that specifically binds to a target DNA of a human dipeptidyl peptidase-4 (DPP4) gene, and (iii) a cationic polymer; wherein the nano-liposome carrier encapsulates the hybrid CRISPR complex.

In these methods, the metal chelating lipid can be selected from the group consisting of: DOGS-NTA-Ni, DMPE-DTPA-Gd, and DMPE-DTPA-Cu, as defined herein, the lecithin can be or include α-phosphatidylcholine, and the cationic polymer can be poly-L-lysine, polyamidoamine, poly[2-(N,N-dimethylamino)ethyl methacrylate], chitosan, poly-L-ornithine, cyclodextrin, histone, collagen, dextran, and/or polyethyleneimine (PEI).

In these methods, the guide RNA can be or include the nucleic acid sequence UUUGGGCCAUUUGGGGAGUU (SEQ ID NO: 1) and the target DNA can be or include the nucleic acid sequence AACTCCCCAAATGGCCCAAA (SEQ ID NO:5). Alternatively, the guide RNA can be or include the nucleic acid sequence GUCCG-GUUUCGCCAGCUUUU (SEQ ID NO:2) and the target DNA can be or include the nucleic acid sequence AAAAGCTGGCGAAACCGGAC (SEQ ID NO:6).

In another aspect, the disclosure relates to methods for producing a nano-liposome carrier compositions as described herein. These methods include mixing a CRISPR-associated protein 9 (Cas9) protein and a guide RNA that specifically binds to a target DNA of a human dipeptidyl peptidase-4 (DPP4) gene to produce a hybrid CRISPR complex; mixing a lecithin, a metal chelating lipid, and a cholesterol in chloroform to produce a lipid film composition; mixing the hybrid CRISPR complex with the lipid film composition to produce a lipid/CRISPR mixture and applying ultrasonic waves to the lipid/CRISPR mixture; freezing and thawing the lipid/CRISPR mixture; re-applying ultrasonic waves to the lipid/CRISPR mixture for a time sufficient to form nano-liposomes encapsulating the hybrid CRISPR complex; centrifuging the lipid/CRISPR mixture for a time sufficient to precipitate nano-liposomes encapsulating the hybrid CRISPR complex; and collecting precipitated nano-liposomes encapsulating the hybrid CRISPR complex.

These methods of manufacture can further include mixing a cationic polymer with the hybrid CRISPR complex, and/or the Cas9 protein and guide RNA can be mixed at a molar ratio of 1:1-3. In some embodiments, the lecithin, the metal chelating lipid, and the cholesterol are mixed at a molar ratio of 1.5-2.5:0.5-1.5:0.1-0.5. In certain embodiments, the freezing and thawing are performed two to six times or more, e.g., 2, 3, 4, 5, 6, or more times.

In some embodiments, the lecithin, metal chelating lipid, and cholesterol are mixed in the chloroform to produce a lipid film composition for about 10, 15, or 20 minutes under conditions to allow evaporation of the chloroform.

In certain embodiments, the ultrasonic waves are applied to the lipid/CRISPR mixture, e.g., in a bath sonicator, at about 25° C., for about 5, 10, 15, or 20 minutes. In various embodiments, the ultrasonic waves are re-applied to the lipid/CRISPR mixture for about one, two, or three minute at a low temperature, e.g., about 4° C. In some embodiments, the lipid/CRISPR mixture is centrifuged at about 10,000 g, e.g., 7500 g, 8500 g, 9000 g, 10,000 g, 12,500 g, or 15,000 g, for about two, three, four, five, six, or seven minutes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF DRAWINGS

FIG. 8B—protein expression of DPP4; FIG. 8C—DPP4 activity confirmation).

DETAILED DESCRIPTION

Figure 1A:
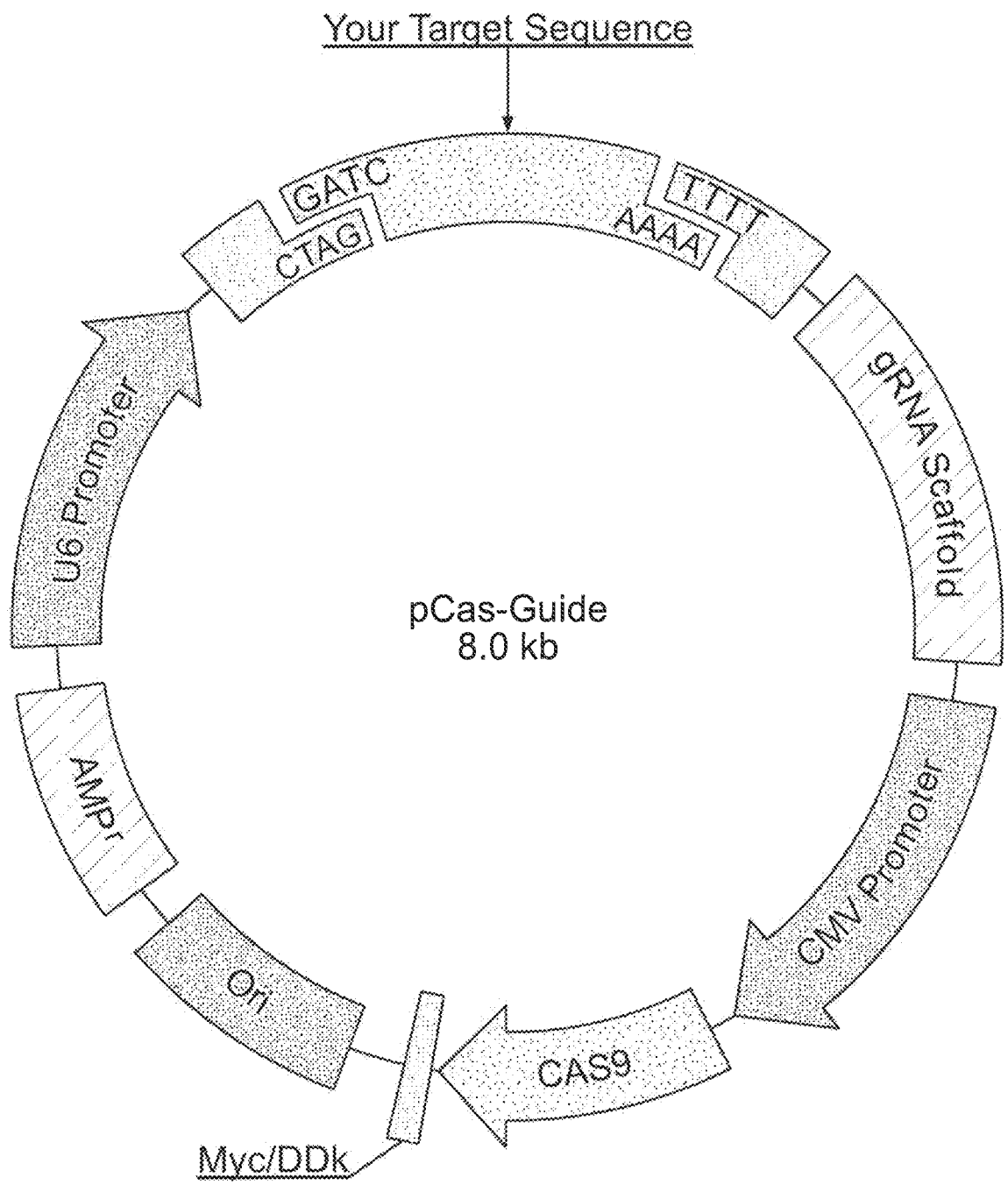
FIG. 1A illustrates one example of a plasmid that can be used to generate a guide RNA for use in the methods described herein (Source: Internet at origene.com/CRISPR-CAS9/Detail.aspx? sku=GE100001).

The present invention relates to nano-liposome carrier compositions containing a hybrid of Cas9 protein and a guide RNA. More specifically, the present invention relates to nano-liposome carrier compositions that encapsulate a hybrid of Cas9 protein and a guide RNA that specifically hybridizes to a target DNA.

The Cas9 protein can be obtained from a cell or a bacterial strain transformed with pET28a/Cas9-Cys plasmid (in which Cas9-Cys is inserted in a pET28a(+) vector) having the structure described herein. For example, the Cas9 protein can be overexpressed and obtained by transforming a pET28a/Cas9-Cys plasmid in *E. coli*.

The guide RNA is designed to suppress expression of a target DNA. Guide RNAs that can be utilized in the present invention include SEQ ID NO: 1 or 2, below. A nano-liposome carrier composition including the guide RNA of SEQ ID NO: 1 or 2 below can function to alleviate or treat type 2 diabetes by suppressing expression of dipeptidyl peptidase-4 (DPP4).

SEQ ID NO: 1:
UUUGGGCCAUUUGGGGAGUU

SEQ ID NO: 2:
GUCCGGUUUCGCCAGCUUUU

The guide RNA of SEQ ID NO: 1 is derived from a partial DNA base sequence of human (*Homo sapiens*) DPP4 of SEQ ID NO: 3 below, and targets and specifically binds to a partial DNA base sequence of DPP4 of SEQ ID NO: 5 below (SEQ ID NO: 3 and SEQ ID NO: 5 have complementary base sequences). The guide RNA of SEQ ID NO: 2 is derived from a partial DNA base sequence of DPP4 of SEQ ID NO: 4 below, and targets and specifically binds to a partial DNA base sequence of DPP4 of SEQ ID NO: 6 below (SEQ ID NO: 4 and SEQ ID NO: 6 have complementary base sequences).

SEQ ID NO: 3:
TTTGGGCCATTTGGGGAGTT

SEQ ID NO: 4:
GTCCGGTTTCGCCAGCTTTT

SEQ ID NO: 5:
AACTCCCCAAATGGCCCAAA

SEQ ID NO: 6:
AAAAGCTGGCGAAACCGGAC

In addition, the present invention provides nano-liposomes for experiments in an animal model, and the nano-liposomes for an animal experiment include guide RNA of SEQ ID NO: 7 or 8. A mouse (*Mus musculus*) can be used as the study or model animal.

SEQ ID NO: 7:
UCAAGUCCUACUCUUUGUGG

SEQ ID NO: 8:
CCAAUAGUUCUGCUGAGCAA

The guide RNA of SEQ ID NO: 7 is derived from a partial DNA base sequence of DPP4 of SEQ ID NO: 9 below, and targets a partial DNA base sequence of DPP4 of SEQ ID NO: 11 below (SEQ ID NO: 9 and SEQ ID NO: 11 have complementary base sequences). The guide RNA of SEQ ID NO: 8 is derived from a partial DNA base sequence of DPP4 of SEQ ID NO: 12 below, and targets a partial DNA base sequence of DPP4 of SEQ ID NO: 12 below (SEQ ID NO: 10 and SEQ ID NO: 12 have complementary base sequences).

SEQ ID NO: 9:
TCAAGTCCTACTCTTTGTGG

SEQ ID NO: 10:
CCAATAGTTCTGCTGAGCAA

```
SEQ ID NO: 11:
CCACAAAGAGTAGGACTTGA

SEQ ID NO: 12:
TTGCTCAGCAGAACTATTGG
```

After the guide RNA base sequence of the SEQ ID NO: 1 or 2 and the guide RNA base sequence of SEQ ID NO: 7 or 8, a scaffold sequence can be included to form a composite with Cas9 protein. Herein, the type of the scaffold base sequence is not particularly limited, and any typical base sequence used in the production of guide RNA can be used.

Accordingly, a guide RNA applied to the nano-liposome of the present invention for use in human patients can include:

```
SEQ ID NO: 13:
UUUGGGCCAUUUGGGGAGUUGUUUUAGAGCU

AGAAAUAGCAAGUUAAAAUAAGGCUAGUCCGUUAUCAACUUGAAAAAGU

GGCACCGAGUCGGUGCUUUUUUU (wherein the underlined sequence is SEQ ID NO: 1)
or

SEQ ID NO: 14:
GUCCGGUUUCGCCAGCUUUUGUUUUAGAGCU

AGAAAUAGCAAGUUAAAAUAAGGCUAGUCCGUUAUCAACUUGAAAAAGU

GGCACCGAGUCGGUGCUUUUUUUU (wherein the underlined sequence is SEQ ID NO: 2),
and for an animal model, a nano-liposome in which the
following sequences can be used:
SEQ ID NO: 15:
UCAAGUCCUACUCUUUGUGGGUUUUAGAGCU

AGAAAUAGCAAGUUAAAAUAAGGCUAGUCCGUUAUCAACUUGAAAAAGU

GGCACCGAGUCGGUGCUUUUUUU (wherein the underlined sequence is SEQ ID NO: 7)
or,

SEQ ID NO: 16:
CCAAUAGUUCUGCUGAGCAAGUUUUAGAGC

UAGAAAUAGCAAGUUAAAAUAAGGCUAGUCCGUUAUCAACUUGAAAAAG

UGGCACCGAGUCGGUGCUUUUUUUU (wherein the underlined sequence is SEQ ID NO: 8).
```

A DNA base sequence of SEQ ID NO: 5 or 6 targeted by the guide RNA of SEQ ID NO: 1 or 2 is a base sequence present between Exon 1 and Exon 2 of human DPP4 (*Homo sapiens* Chromosome 2, Gene bank No. NC_000002.12), and DNA between the Exon 1 and the Exon 2 is cut using the guide RNA of SEQ ID NO: 1 or 2.

A guide RNA of SEQ ID NO: 7 targets and directs cutting of DNA of Exon 3 of mouse DPP4 (*Mus musculus* strain C57BL/6J Location: Chromosome 2, Gene bank No. NC_000068.7), and a guide RNA of SEQ ID NO: 8 that targets and directs cutting of Exon 2 of mouse DPP4.

The guide RNA of SEQ ID NO: 1 or 2 or the SEQ ID NO: 7 or 8 can be synthesized by in vivo transcription using T7 RNA polymerase.

A composite can be produced by combining a cationic polymer with the hybrid of Cas9 protein and a guide RNA, and the cationic polymer can be any one or more polymers selected from the group including or consisting of poly-L-lysine, polyamidoamine, poly[2-(N,N-dimethylamino)ethyl methacrylate], chitosan, poly-L-omithine, cyclodextrin, histone, collagen, dextran, and polyethyleneimine (PEI).

Zuris et al., "Cationic lipid-mediated delivery of proteins enables efficient protein-based genome editing in vitro and in vivo," Nat. Biotechnol., 33(1), 73-80 (2015) describes various cationic lipids for use in delivery of protein-based genome editing components into cells, and is incorporated herein by reference in its entirety.

The nano-liposomes can include lecithin (α-phosphatidylcholine), cholesterol, and metal chelating lipids, and thus the lecithin, the cholesterol, and the metal chelating lipids can constitute a membrane for forming a nano-liposome.

Lecithin is widely distributed in the animal/plant kingdom, has excellent biocompatibility, and its stability has already been verified. Thus, lecithin is widely utilized in food and drug delivery techniques. Moreover, lecithin can be used as a material for facilitating size adjustment and modification of nano-liposomes described herein.

The metal chelating lipid can be one or more lipids selected from a group including or consisting of DOGS-NTA-Ni lipid, DMPE-DTPA-Gd lipid, and DMPE-DTPA-Cu lipid, wherein the DOGS-NTA-Ni lipid is a lipid having a chemical structure shown in Chemical Formula 1 below,

[Chemical Formula 1]

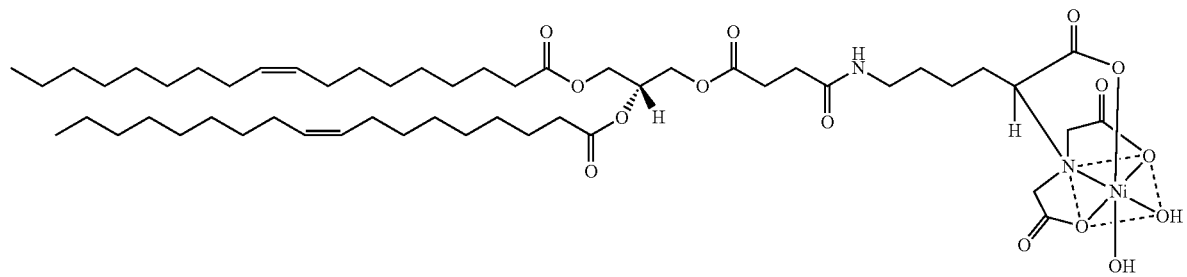

and is referred to as 1,2-dioleoyl-sn-glycero-3-[(N-5-amino-1-carboxypentyl) iminodiacetic acid) succinyl] (nickel salt) ["DOGS-NTA-Ni"].

The DMPE-DTPA-Gd lipid is a lipid having a chemical structure shown in Chemical Formula 2 below,

[Chemical Formula 2]

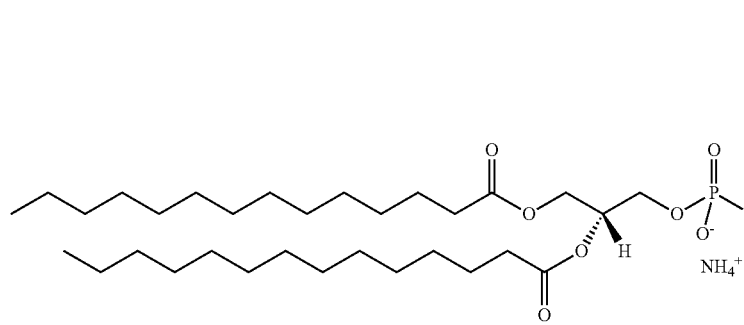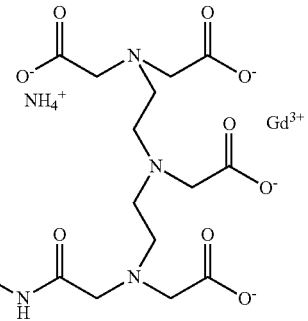

and is referred to as 1,2-dimyristoyl-sn-glycero-3-phospho-ethanolamine-N-diethylenetriaminepentaacetic acid (gadolinium salt) ["DMPE-DTPA-Gd"].

The DMPE-DTPA-Cu lipid is a lipid having a chemical structure shown in Chemical Formula 3 below,

[Chemical Formula 3]

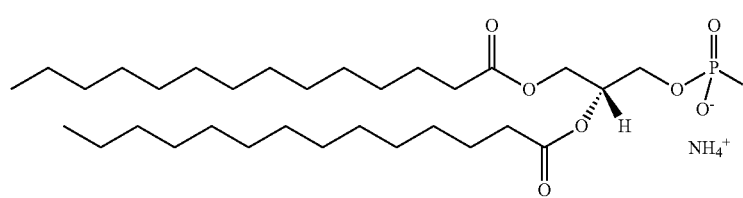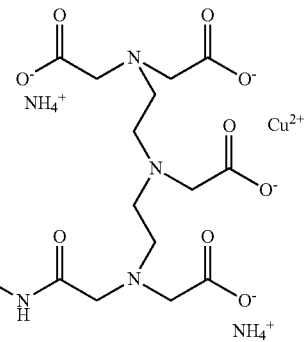

and is referred to as 1,2-dimyristoyl-sn-glycero-3-phospho-ethanolamine-N-diethylenetriaminepentaacetic acid (copper salt) ["DMPE-DTPA-Cu"].

The metal chelating lipid, such as the DOGS-NTA-Ni lipid, can perform the role of causing Cas9 protein (including the His-Tag) to be effectively encapsulated in a nano-liposome by utilizing the affinity of $Ni^{2+}$ and the His-Tag (6× histidine) used in a protein purification method. More specifically, the DOGS-NTA-Ni has a structure having one double bond in 18 carbons and can form lipids with lecithin, and $Ni^{2+}$ is attached to the end thereof. Thus, two His-tags attached to Cas9 protein bond with one $Ni^{2+}$, thereby causing the Cas9 protein to become more effectively encapsulated in a nano-liposome.

In the nano-liposomes of the present invention, the Cas9 protein bound with a guide RNA, e.g., including a base sequence of SEQ ID NO: 1 and the Cas9 protein bound with a guide RNA, e.g., including a base sequence of SEQ ID NO: 2 can exist mixed together. Also, in a nano-liposome for an animal experiment, the Cas9 protein bound with a guide RNA, e.g., including a base sequence of SEQ ID NO: 7 and the Cas9 protein bound with a guide RNA, e.g., including a base sequence of SEQ ID NO: 8 can exist mixed together.

The nano-liposomes can have a particle size of 10 to 2,000 nm. When the size of the nano-liposomes is less than 10 nm, it may be difficult for a hybrid of Cas9 protein and guide RNA specific to target DNA to be encapsulated in the nano-liposomes. In addition, stability of such liposomes of less than 10 nm in diameter is lower when introduced into the body of an animal or human subject than larger nano-liposomes. Thus, it is not preferable for the size of the nano-liposomes to be less than 10 nm. Moreover, it is not preferable for particle size of the nano-liposome to be greater than 2,000 nm because, again, stability of such larger liposomes may be lower when introduced into the body of an animal or human subject.

The nano-liposome of the present invention can be stably dispersed for several hours or more in neutral water, cell culture medium, blood, and the like.

The present invention provides compositions for alleviating or treating type 2 diabetes, wherein the compositions contain the nano-liposome carrier compositions. With respect to the compositions for alleviating or treating type 2 diabetes, the nano-liposome carrier compositions contain, as a guide RNA specific to target DNA, a guide RNA for suppressing expression of DPP4. The DPP4 gene is related to diabetes regulation, and it is known that drugs considered to be diabetes therapeutic agents, such as sitagliptin, have an excellent effect in suppressing expression of DPP4.

The present invention also provides methods for producing a nano-liposome carrier composition, as described below. In some embodiments, the methods include a first step of producing a hybrid of Cas9 protein and guide RNA that is specific to target DNA, and producing a lipid film composition by mixing lecithin, a metal chelating lipid, and cholesterol in chloroform; a second step of adding a hybrid of Cas9 protein and a guide RNA which is specific to target DNA to the lipid film composition, and treating the same by ultrasonic waves; a third step of freezing and thawing the lipid film composition treated by the ultrasonic waves, and re-treating the same by sonication; and a fourth step of centrifuging the lipid film composition treated by sonication in the third step, and collecting pelleted materials.

A composite may be produced by combining a cationic polymer with the hybrid of the first step, and the cationic polymer may be preferably one or more selected from poly-L-lysine, polyamidoamine, poly[2-(N,N-dimethylamino)ethyl methacrylate], chitosan, poly-L-ornithine, cyclodextrin, histone, collagen, dextran, and polyethyleneimine.

In the first step, Cas9 protein and a guide RNA can be mixed at a molar ratio of 1:1-3. When a composite is formed by adding a cationic polymer to the hybrid of Cas9 protein and a guide RNA, Cas9 protein:guide RNA:cationic polymer may be mixed at a molar ratio of 1:1-3:30-70, and preferably at a molar ratio of 1:2:50.

Herein, the lecithin, the metal chelating lipid, and the cholesterol of the first step can be mixed at a molar ratio of 1.5-2.5:0.5-1.5:0.1-0.5, e.g., at a molar ratio of 1.8-2.2:0.8-1.2:0.2-0.3, for example, at a molar ratio of 2:1:0.3.

Herein, the freezing and thawing step of the third step can be performed 3-6 times. By repeatedly performing the step of freezing and thawing a lipid film composition, a nano-liposome dispersion with a more uniform size can be produced, and the drug encapsulation efficiency of the nano-liposome can be improved. Since performing the freezing and thawing step more than 6 times can lower the nano-liposome encapsulation efficiency, it is preferable that the freezing and thawing step is performed no more than 6 times.

When producing the nano-liposome of the present invention, since the metal chelating lipid has a negative charge (−), a liposome may not effectively encapsulate due to reacting with a negative charge (−) of a hybrid of Cas9 and guide RNA. Accordingly, to overcome this, a composite is produced in which a cationic polymer having a positive charge (+) is combined with a hybrid of Cas9 and a guide RNA to increase nano-liposome encapsulation.

The present invention also provides pharmaceutical compositions containing the nano-liposome carrier compositions in the form of a powder, a granule, a pill, a capsule, a suspension, an emulsion, a syrup, an aerosol, and any other conventional methods of the like. Carriers, excipients, and diluting agents included in the pharmaceutical composition may include, for example, lactose, dextrose, sucrose, sorbitol, mannitol, xylitol, erythritol, maltitol, starch, acacia rubber, alginate, gelatine, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

When formulating the pharmaceutical composition, a typically used diluting agent or excipient, such as a filler, a bulking agent, a binder, a wetting agent, a disintegrating agent, a surfactant, and the like is used. Solid formulations for oral administration include tablets, pills, powders, granules, capsules, and the like. Such solid formulations are produced by mixing the composition of the present invention with one or more excipients, such as starch, calcium carbonate, sucrose or lactose, gelatine, and the like. Moreover, in addition to simple excipients, lubricants such as magnesium stearate and talc are also used. Liquid formulations for oral administration include suspensions, solutions for ingestion, emulsions, syrups, and the like.

In addition to water and liquid paraffin, which are commonly used simple diluting agents, various excipients, such as wetting agents, sweeteners, flavouring agents, preservatives, and the like may be included. Formulations for non-oral administration include sterilized solutions, non-aqueous solvents, suspensions, emulsions, freeze-dried formulation, and suppositories. Non-aqueous agents and suspensions include propylene glycol, polyethylene glycol, plant oils such as olive oil, injectable esters such as ethylolate, and the like. As a base material for the suppository, witepsol, macrogol, tween 61, cacao butter, laurinum, and glycerogeratin and the like may be used.

An administration amount or dosage of the pharmaceutical compositions described herein may differ according to the age, sex, and weight of a treatment subject, the specific disease or pathological state to be treated, the severity of a disease or pathological state, the administration pathway, and the judgement of a prescriber. Determining the proper dosage based on such factors is within the abilities of a person skilled in the art. In general, dosages are in the range of 0.01 to approximately 2000 mg/kg/day of the compositions described herein, e.g., in the range of 1 to 500 mg/kg/day. Administration may be performed once a day, and can also be performed in portions several times a day. These general dosages do not limit the scope of the present invention in any way.

The pharmaceutical compositions of the present invention can be administered to mammals such as mice, dogs, cats, monkeys, livestock, and humans through various routes. All known methods of administration can be used. For example, administration can be oral, rectal, intravenous, intramuscular, subcutaneous, endometrial, or through cerebral arteries.

EXAMPLES

Hereinafter, Examples of the present invention will be described in detail. However, the present invention is not limited to the Examples explained herein, and can be embodied in various forms. Rather, Examples are provided to make the content introduced herein more thorough and complete, to sufficiently communicate the concept of the present invention to a person skilled in the art.

Example 1. Guide RNA Production and Cas9 Protein Purification

Example 1-1. Production of Guide RNA Using DPP4 as a Target Gene

A guide RNA using DPP4 as a target gene was produced by using an in vitro transcription method utilizing T7 RNA polymerase (New England Biolabs, Ipswich, Mass.). To this end, a DNA template of 140 b.p. was produced through a PCR method by using four "69 mer forward primer" guides including the T7 promoter base sequence of Table 1 and a 20 b.p. base sequence of DPP4 (human or mouse)

SEQ ID NO: 3:
TTTGGGCCATTTGGGGAGTT,

SEQ ID NO: 4:
GTCCGGTTTCGCCAGCTTTT,

SEQ ID NO: 9:
TCAAGTCCTACTCTTTGTGG,
or

SEQ ID NO: 10:
CCAATAGTTCTGCTGAGCAA, one "21 mer reverse primer" including a scaffold base sequence to be connected to the guide RNA, and a plasmid Cas guide vector (Origene). The guide RNA was produced by including the DNA template, an rNTP mixture, a T7 RNA polymerase, and an RNase inhibitor through a 2-hour transcription reaction at 37° C. and RNA purity was increased through an RNA refining step.

In Table 1 below, the underlined nucleic acid sequence corresponds to the T7 promoter base sequence and the bold font nucleic acid sequences correspond to a section of the nucleotide sequence for recognizing and targeting a DPP4 gene. This section is synthesized into a guide RNA by recognizing a template (plasmid Cas guide vector) of a scaffold base sequence, and the sequence of the guide RNA that is ultimately produced and the base sequence have the same base sequence structure (with U substituted for T).

As shown in Table 1, GTTTAGAGCTAGAAATAGCA (SEQ ID NO: 21) following a Forward primer is part of a scaffold base sequence. The template of a scaffold base sequence is included in a plasmid Cas guide vector.

The structure of the plasmid Cas guide vector used in this experiment is shown in FIG. 1A.

TABLE 1

| forward primer | Human DPP4 sgRNA 1_F | GCGGCCTCTAATACGACTCACTATAGGGTTTGGGCCATTTGGGGAGTTGTTTTAGA GCTAGAAATAGCA (SEQ ID NO: 13) |
|---|---|---|
| | Human DPP4 sgRNA 2_F | GCGGCCTCTAATACGACTCACTATAGGGGTCCGGTTTCGCCAGCTTTTGTTTTAGA GCTAGAAATAGCA (SEQ ID NO: 14) |
| | Mouse DPP4 sgRNA 1_F | GCGGCCTCTAATACGACTCACTATAGGGTCAAGTCCTACTCTTTGTGGGTTTTAGAG CTAGAAATAGCA (SEQ ID NO: 15) |
| | Mouse DPP4 sgRNA 2_F | GCGGCCTCTAATACGACTCACTATAGGGCCAATAGTTCTGCTGAGCAAGTTTTAGA GCTAGAAATAGCA (SEQ ID NO: 16) |
| reverse primer (sg RNA R) | | AAAAGCACCGACTCGGTGCCA (SEQ ID NO: 22) |

A guide RNA having a base sequence from Table 2 below was produced from the above experiment. In Table 2, the underlined nucleic acid sequences are target gene sequences.

TABLE 2

| SEQ ID NO: 17 (human DPP4 target) | UUUGGGCCAUUUGGGGAGUUGUUUUAGAGCUAG AAAUAGCAAGUUAAAAUAAGGCUAGUCCGUUAU CAACUUGAAAAAGUGGCACCGAGUCGGUGCUUU UUUUU |
|---|---|

TABLE 2-continued

| SEQ ID NO: 18 (human DPP4 target) | GUCCGGUUUCGCCAGCUUUUGUUUUAGAGCUAG AAAUAGCAAGUUAAAAUAAGGCUAGUCCGUUAU CAACUUGAAAAAGUGGCACCGAGUCGGUGCUUU UUUUU |
|---|---|
| SEQ ID NO: 19 (mouse DPP4 target) | UCAAGUCCUACUCUUUGUGGGUUUUAGAGCUAG AAAUAGCAAGUUAAAAUAAGGCUAGUCCGUUAU CAACUUGAAAAAGUGGCACCGAGUCGGUGCUUU UUUUU |
| SEQ ID NO: 20 (mouse DPP4 target) | CCAAUAGUUCUGCUGAGCAAGUUUUAGAGCUAG AAAUAGCAAGUUAAAAUAAGGCUAGUCCGUUAU CAACUUGAAAAAGUGGCACCGAGUCGGUGCUUU UUUUU |

Figure 1B:
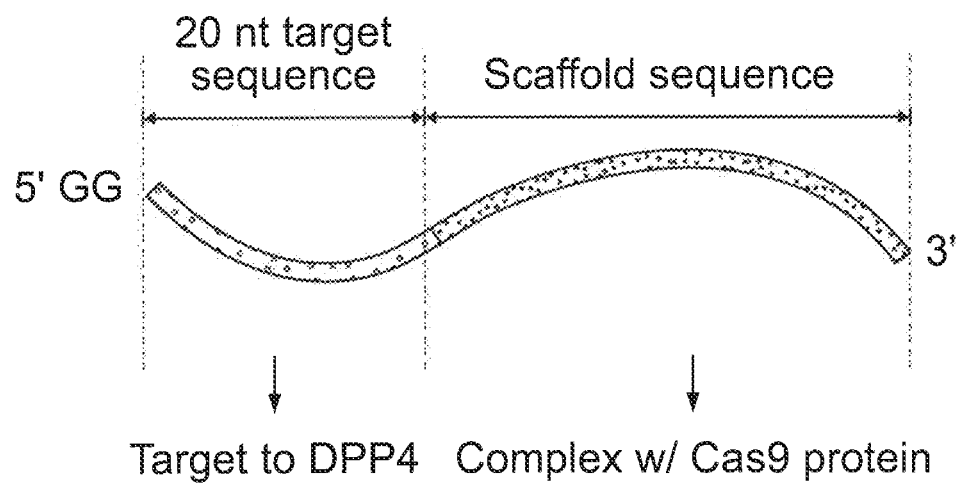
FIG. 1B illustrates a schematic base sequence structure of guide RNA (sgRNAs) in a single-strand state that can be used in the present invention.

A schematic of the general structure of the guide RNA (sgRNA) of Table 2 in a single-strand state produced as described herein is illustrated in FIG. 1B.

The guide RNA that was ultimately produced recognizes: AACTCCCCAAATGGCCCAAA (SEQ ID NO: 5) or AAAAGCTGGCGAAACCGGAC (SEQ ID NO: 6) of a human DPP4 gene as a target, recognizes CCACAAAGAGTAGGATTGA (SEQ ID NO: 11) or TGCTCAGCAGAACTATGG (SEQ ID NO: 12) of a mouse DPP4 gene as a target, and suppresses expression of each DPP4 gene.

Example 1-2. Purification of Cas9 Protein

Figure 1C:
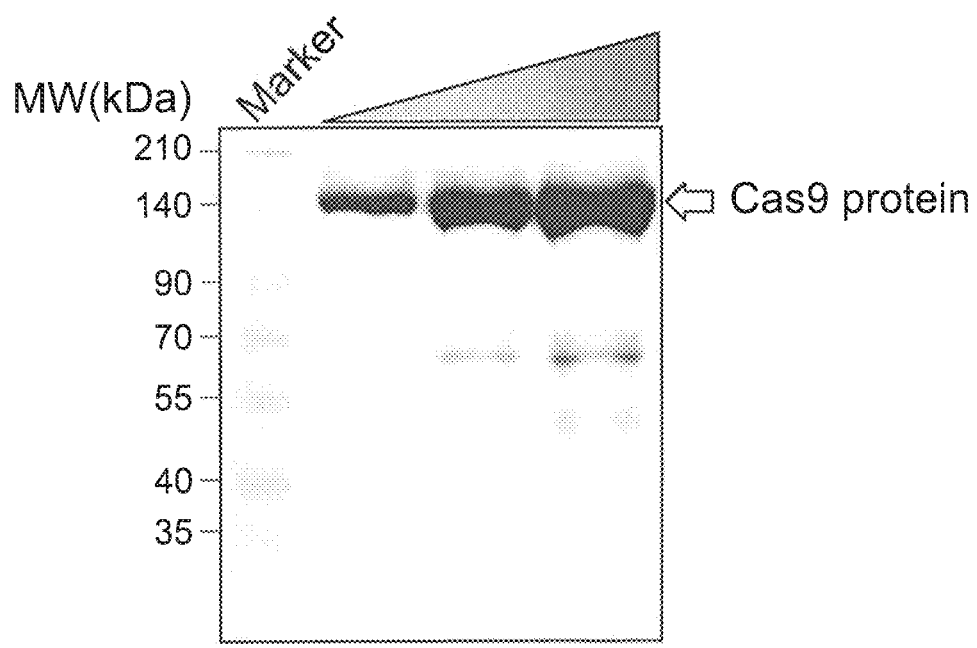
FIG. 1C is an image of a sodium dodecyl sulphate polyacrylamide gel electrophoresis (SDS-PAGE) gel after purifying a Cas9 protein produced as described in Example 1.
Figure 1D:
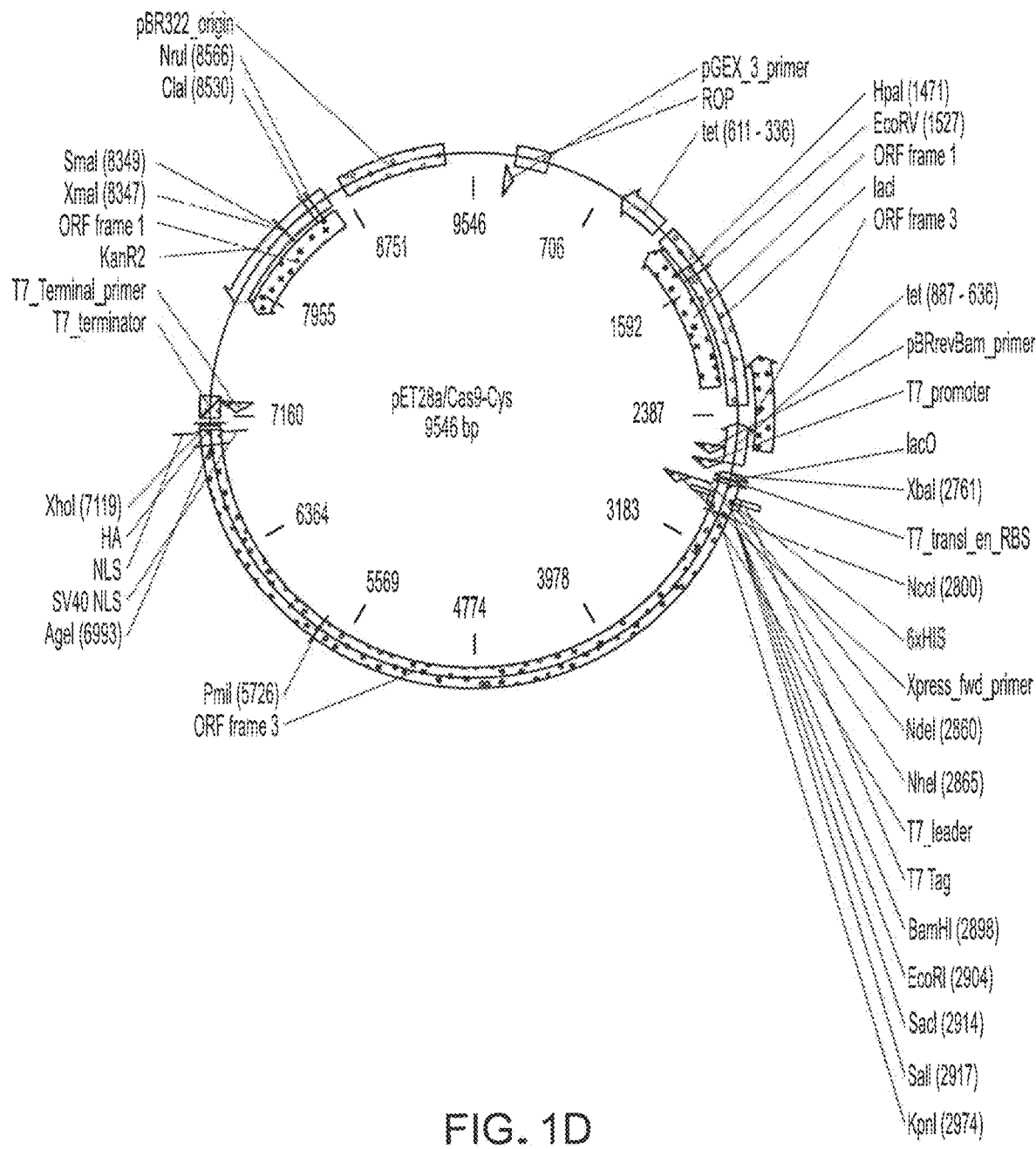
FIG. 1D illustrates an example of a pET28a/Cas9-Cys plasmid that can be used to generate a Cas9 protein as used in the methods described herein and in the examples (Source: Addgene, Internet at addgene.org).

As shown in FIG. 1D, a pET28a/Cas9-Cys plasmid (Addgene plasmid #53261) was transformed into E. coli (DH5α), and Cas9 protein was overexpressed in 0.5 mM isopropyl β-D-1-thiogalactopyranoside (IPTG) at 28° C. E. coli in which Cas9 protein was overexpressed was sonicated for about 5 minutes in a lysis buffer (20 mM Tris-Cl at pH 8.0, 300 mM NaCl, 20 mM imidazole, 1× protease inhibitor cocktail, 1 mg/mL lysozyme). A pulverized material obtained through sonication was centrifuged (at 10,000-13,000 g), and thereby a supernatant including protein was obtained. Cas9 protein included in the supernatant was separated through a Ni-NTA agarose bead extraction method (elution buffer: 20 mM Tris-Cl at pH 8.0, 300 mM NaCl, 300 mM imidazole, 1× protease inhibitor cocktail). Then, an isolate, suspended in a storage buffer (50 mM Tris-HCl at pH 8.0, 200 mM KCl, 0.1 mM EDTA, 1 mM DTT, 0.5 mM PMSF, 20% glycerol), was dialyzed thereby removing imidazole, and the protein concentration was quantified (using a BCA method). Here, the Cas9 protein obtained by dialysis was observed through SDS-PAGE performed concentration-dependently, and it was confirmed that the Cas9 protein was effectively generated (see the image in FIG. 1C).

Example 2. Production of a Nano-Liposome

A composite was produced by mixing the Cas9 protein produced in Example 1, a guide RNA, and polyethyleneimine at a molar ratio of 1:2:50. Here, SEQ ID NOs: 13-16 including scaffold base sequences were used as the guide RNA. Next, lecithin (Sigma Aldrich), DOGS-NTA-Ni lipid (Avanti polar lipid), and cholesterol (Sigma Aldrich) were mixed at a molar ratio of 2:1:0.3 on chloroform, and were made into a lipid film by utilizing a rotary evaporator. Here, the composite (hybrid) of Cas9 protein/guide RNA/polyethyleneimine (250 nM) was added into the lipid film mixture (1 mM lecithin, 2 mL) and mixed while sonicating for about 2 to 6 minutes. A freezing and thawing step (freeze thaw cycle) utilizing liquid nitrogen was performed five times, followed by sonication for a few minutes. Thereby, nano-liposomes having a smaller size and in a uniform state was produced. Then, centrifugation (10,000-13,000 g) was used to collect only pelleted materials, and thereby the nano-liposome of the present invention was obtained. The nano-liposomes were mixed with a progress buffer (cell culturing culture medium or phosphate buffered saline [PBS]) to a concentration of 10.75 mg/mL and were used in a subsequent experiment.

Figure 2:
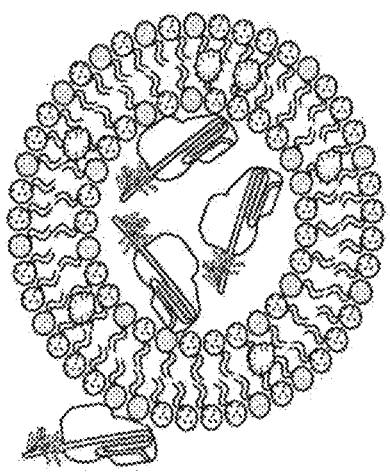
FIG. 2 is a schematic illustration of a nano-liposome of Example 2. The nano-liposome consists of lecithin, cholesterol, and metal chelating lipid, and has encapsulated therein a composition in which polyethyleneimine (PEI) is combined with a hybrid of a Cas9 protein and a guide RNA.
Figure 3:
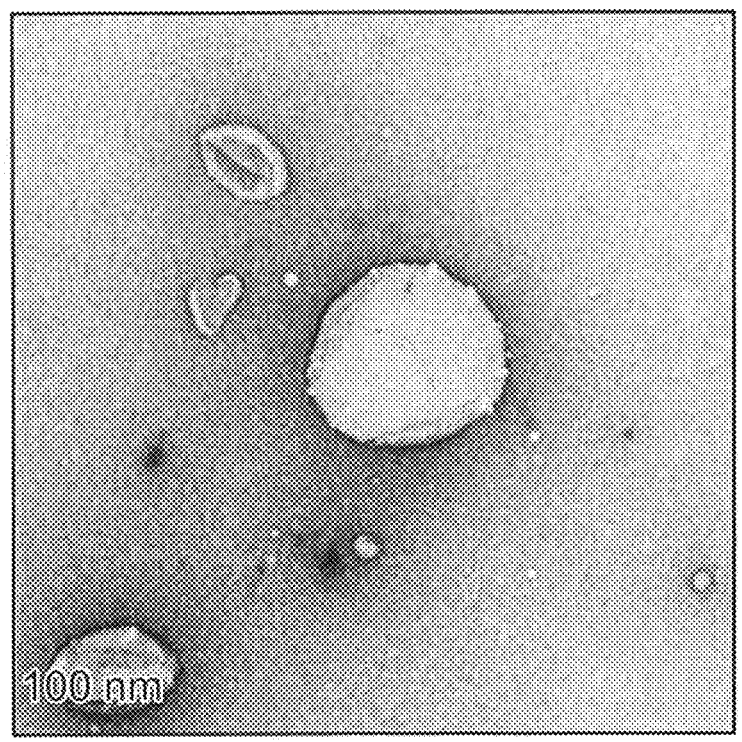
FIG. 3 is a bio-transmission electron microscopy (bio-TEM) image of a nano-liposome of Example 2 as described herein.

A cell treatment group of the nano-liposome produced through such a method was designated "NL(Ni)-Cas9/gDPP4(PEI)," and an animal treatment group was designated "db/db(Cas9/gDPP4)." The nano-liposomes are illustrated in FIG. 2, and an image obtained by photographing the nano-liposome in such a state through bio-TEM is shown in FIG. 3.

A guide RNA of SEQ ID NO: 2 is included in the nano-liposome shown in FIG. 3, and nano-liposomes including a guide RNA of SEQ ID NO: 1, SEQ ID NO: 7, and SEQ ID NO: 8, nano-liposomes including SEQ ID NOs: 1 and 2, or nano-liposomes including SEQ ID NOs: 7 and 8 were also confirmed to have a similarly stable image.

Comparative Example 1. Production of a Nano-Liposome

Nano-liposomes for comparative testing were produced by excluding DOGS-NTA-Ni lipid and mixing only lecithin and cholesterol using the method described in Example 2. Moreover, a step of encapsulating a composite of Cas9 protein/guide RNA/polyethyleneimine in a nano-liposome was excluded, and the nano-liposomes were designated "NL" for cell treatment.

Comparative Example 2. Production of a Nano-Liposome-NL(Ni)

Nano-liposomes for comparative testing were produced by mixing lecithin, cholesterol, and DOGS-NTA-Ni lipid through the same method described in Example 2, other than excluding a step of encapsulating a composite of Cas9 protein/guide RNA/polyethyleneimine in a nano-liposome. The nano-liposome was designated "NL(Ni)" for cell treatment.

Comparative Example 3—Nano-Liposome that does not Include DOGS-NTA-Ni Lipid and Polyethyleneimine (NL-Cas9/gDPP4)

As in Example 1, nano-liposomes for comparative testing were produced by excluding DOGS-NTA-Ni lipid and mixing only lecithin and cholesterol. Then, the step of Example 2 was performed, with the exception that a hybrid of Cas9 protein/guide RNA, instead of the composite of Cas9 protein/guide RNA/polyethyleneimine, was encapsulated in the nano-liposomes. The nano-liposomes were designated "NL-Cas9/gDPP4" for cell treatment.

Comparative Example 4. Nano-Liposome that does not Include Polyethyleneimine (NL(Ni)-Cas9/gDPP4)

Nano-liposomes for comparative testing were produced as in Example 2, with the exception that a hybrid of Cas9 protein/guide RNA, instead of the composite of Cas9 protein/guide RNA/polyethyleneimine, was encapsulated in the nano-liposomes. The nano-liposomes were designated "NL(Ni)-Cas9/gDPP4" for cell treatment.

Experimental Example 1—Confirmation of the State of a Nano-Liposome

Experimental Example 1-1—Confirmation of Encapsulation Efficiency of a Nano-Liposome The total amount of a Cas9 protein at the start of the synthesis of nano-liposomes and the amount of Cas9 protein remaining in a filtrate after the synthesis were measured by a Western blot experiment method, and the encapsulation efficiency of nano-liposomes was thereby confirmed. Here, when the produced nano-liposomes were centrifuged at 13000 rpm by using a centrifuging device, the nano-liposomes settled, and Cas9 protein, which was not encapsulated in the nano-liposomes remains in the supernatant. Thus, the supernatant containing the un-encapsulated Cas9 protein was tested in a Western blot experiment. By comparing the contents of the Cas9 protein remaining in the supernatant remaining after producing the nano-liposome, the encapsulation efficiency of the nano-liposome can be easily confirmed.

Figure 4A:
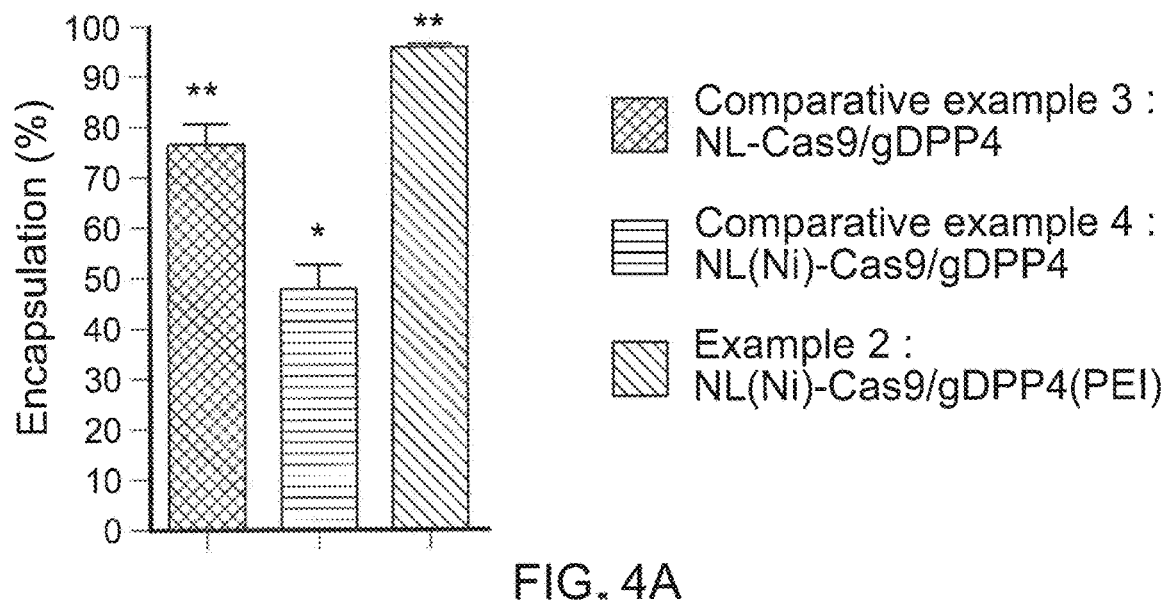
FIG. 4A is a graph showing the encapsulation efficiency of nano-liposomes produced in the present invention.
Figure 4B:
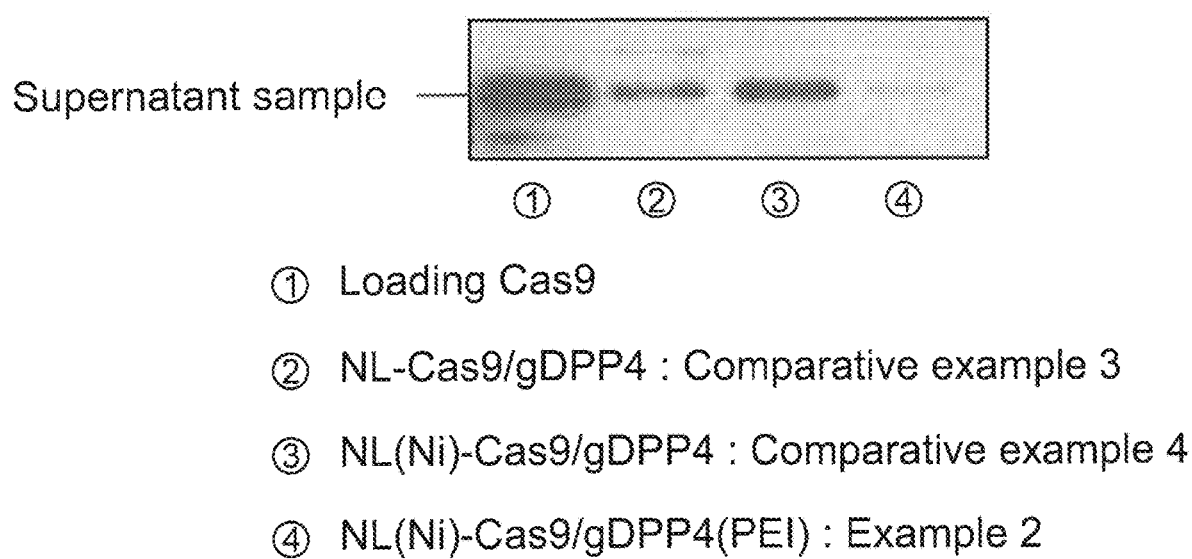
FIG. 4B is a Western blot result showing the Cas9 protein content remaining in a filtrate (upper liquid) after producing a nano-liposome.

According to the encapsulation efficiency results, there was little variation between the different kinds of guide RNAs, and results obtained when the guide RNA of SEQ ID NO: 2 was included is representatively displayed in FIGS. 4A and 4B. FIG. 4A demonstrates that the encapsulation efficiency of a hybrid or a composite including the guide RNA was best in the nano-liposomes of Example 2, and was about 95%.

Experimental Example 1-2—Confirmation of the Surface Charge, Size, and Dispersibility of a Nano-Liposome Surface charge change (zeta potential, mV), size, and dispersibility of nano-liposomes produced in the present invention were measured through dynamic light scattering (DLS). There was little variation in the measured values between different kinds of guide RNA strands, and results obtained when the guide RNA of SEQ ID NO: 2 was included is representatively displayed in FIGS. 5A-5C, wherein the bar graph of FIG. 5A indicates surface charge for Comparative Examples 1-4 and Example 2, the pair of graphs in FIG. 5B show the size in nanometers for Comparative Example 3 and Example 2, and the graph in FIG. 5C shows dispersibility for Comparative Example 3 and Example 2.

Figure 5A:
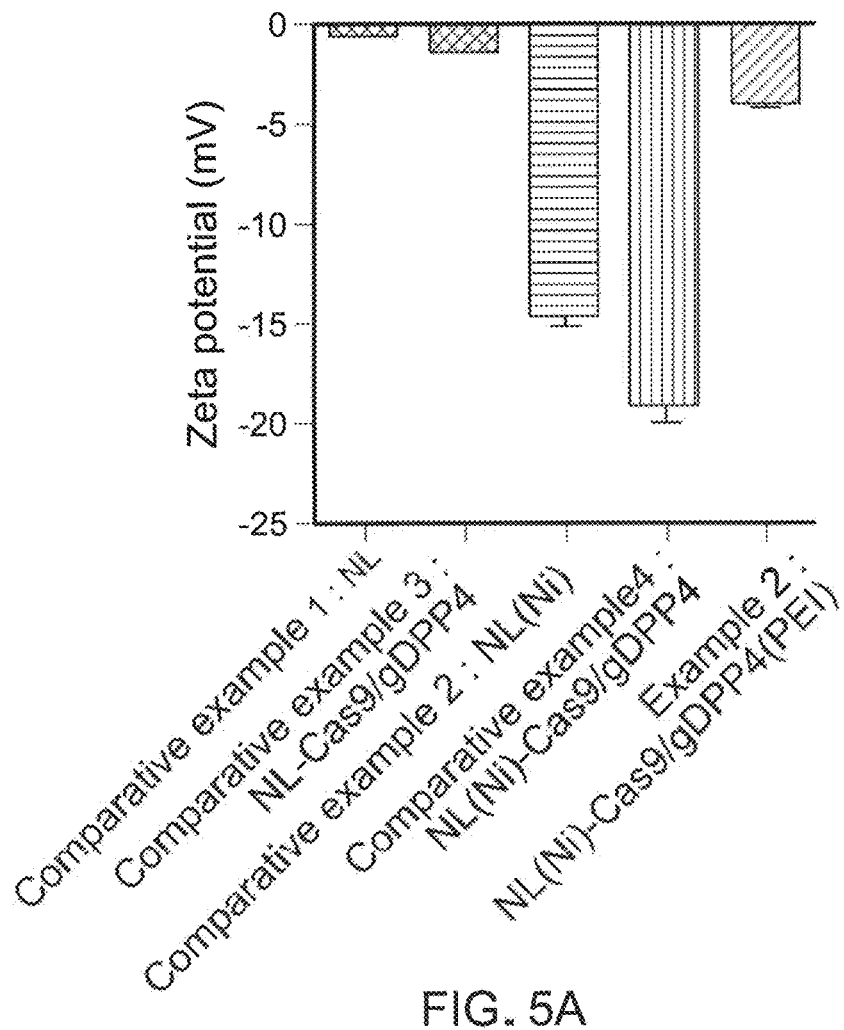
FIGS. 5A to 5C are a series of graphs showing stability results with respect to the surface charge change (zeta potential, mV), size, and dispersibility of nano-liposomes produced according to the methods described herein (surface charge—FIG. 5A, size—FIG. 5B, dispersibility—FIG. 5C).
Figure 5B:
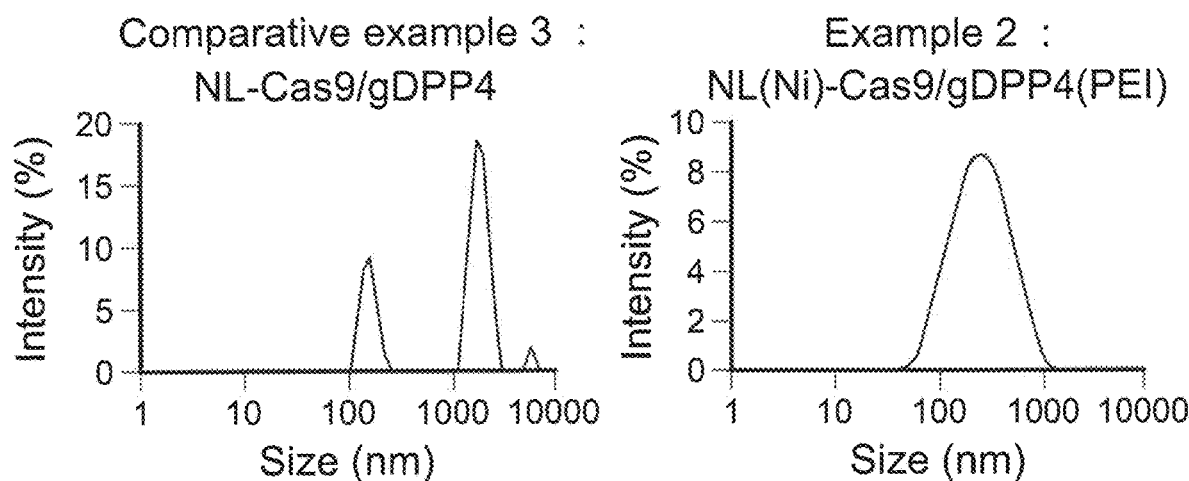
Figure 5C:
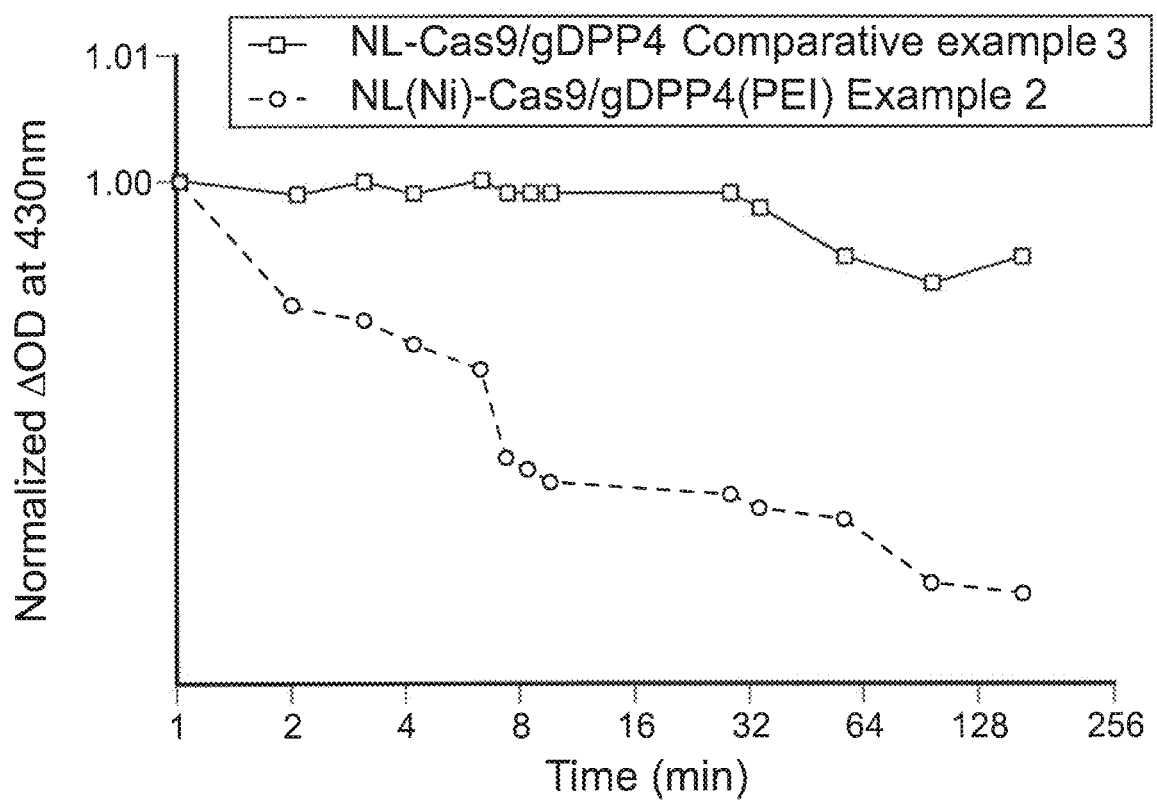

It is advantageous to reduce as far as possible a negatively charged surface charge value in order to transfer a nano-liposome including guide RNA into a cell, and the nano-liposome of Example 2 has a relatively low surface charge value, as seen in FIG. 5A. The nano-liposome of Comparative Example 3 also has a low surface charge, but it was observed that the stability of the nano-liposome is poor, because dispersibility decreases with time. Moreover, with respect to the particle size of a nano-liposome, it was observed that the nano-liposome of Example 2 was produced with a uniform size, but the nano-liposomes of Example 3 did not have a uniform size (two peaks are observed). Although not shown in FIGS. 5B and 5C, the results confirmed that the nano-liposomes of Example 2 were also better than the nano-liposomes of Comparative Example 4 in terms of size uniformity and dispersibility.

Experimental Example 2. Measurement of DPP4 Expression and Activity

Experimental Example 2-1—Confirmation of Mutation of a DPP4 Gene

DNA was extracted from a human liver cancer cell (CNU398) collected after treatment with each nano-liposome (human target) produced in the present invention for 24 hours at a concentration of Cas9:gRNA (74 μg:28 μg), and a template fragment was produced through a PCR method by using a forward primer: GTGAGTGCCGCGC-CACGTACG (SEQ ID NO: 23) and a reverse primer: CTGCAAGCCGAGCAGATCAAG (SEQ ID NO: 24).

Next, the template fragment was inserted in a T-blunt vector by using a T-blunt PCR cloning kit (SolGent Co. Ltd., Seoul, Korea). Then, the sequence of a template fragment part was analyzed by sending a sequencing service request to Bioneer Corp. According to the results, there was little variation resulting from the kind of guide RNA, and a picture showing mutated DNA is representatively shown in FIG. 6 (SEQ ID NO: 25 (WT), SEQ ID NO: 26 (gDPP4), and SEQ ID NO: 27 (18 bp deletion segment of gDPP4), wherein the guide RNA of SEQ ID NO: 2 is included.

Figure 6:
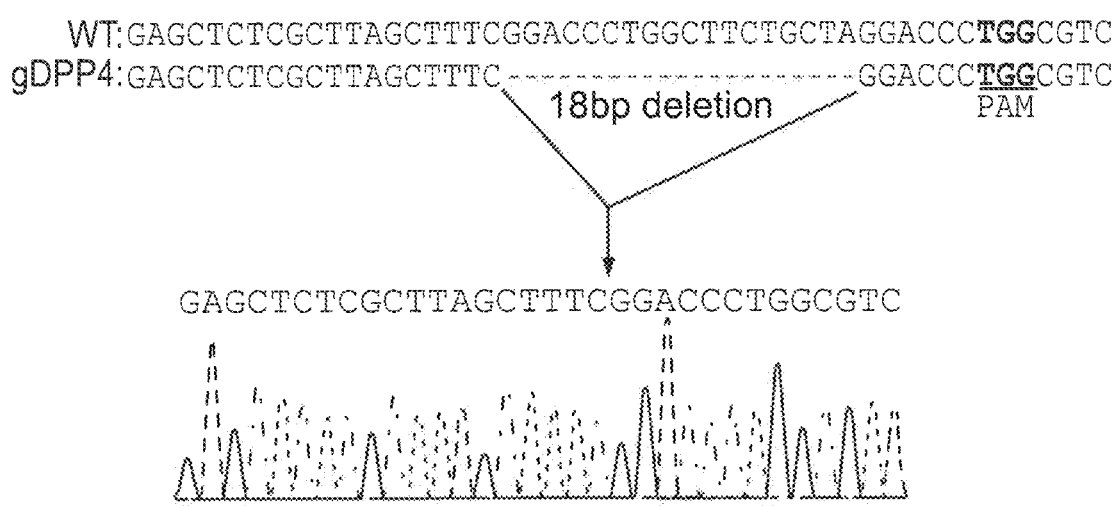
FIG. 6 is a representation showing that the 18 base sequence of a DPP4 gene in a human liver cancer cell has been cut (mutated) compared to a wild type gene (WT) of DPP4, using a nano-liposome prepared as described herein.

FIG. 6 illustrates that the guide RNA recognizes 20-mer base sequences through the nano-liposome of the present invention, and Cas9 protein cuts a protospacer adjacent motif (PAM) (TGG sequence) section. Thus, it is confirmed that 18 DNA base sequences are cut during a step in which cut DNA is autonomously recovered (repaired).

Experimental Example 2-2—DPP4 Expression Measurement I

Figure 7:
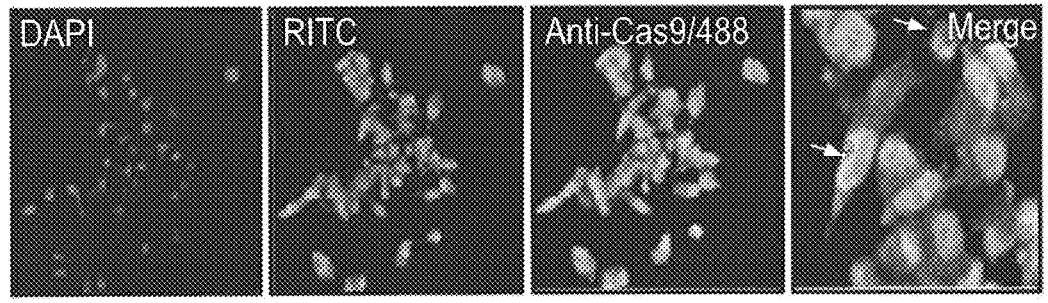
FIG. 7 is a series of confocal fluorescent microscope images, which confirm through a fluorescence immunoassay using RITC and Cas9 antibodies that a nano-liposome of Example 2 marked with rhodamine B isothiocyanate (RITC) was effectively fed into a human liver cancer cell.

The nano-liposome (human target) of Example 2 was marked with rhodamine B isothiocyanate (RITC) and used to treat human liver cancer cells (SNU398). Then, immunostaining was performed, and the resulting confocal fluorescent microscopy picture is shown in FIG. 7. To mark the nano-liposome with RITC, a RITC dye was mixed and encapsulated together in Cas9 protein when producing the nano-liposome. Moreover, to perform immunostaining, Cas9 protein in the cells was marked using a Cas9 primary antibody (rabbit) of CFL-488, and was imaged by a confocal fluorescent microscope. According to the result, there was little variation between the different kinds of guide RNA strands, and a representative result of SEQ ID NO: 2 is shown in FIG. 7.

FIG. 7 shows that RITC and Cas9 protein were effectively introduced into the nucleus of human liver cancer cells through the treatment of the nano-liposome of Example 2.

Experimental Example 2-3—DPP4 Expression Measurement II

Total RNA was extracted by using trizol (Invitrogen—Thermo Fisher Scientific, Carlsbad, Calif.) from human liver cancer cells (SNU398) collected after treatment with each nano-liposome (human target) produced in the present invention at a concentration of Cas9:gRNA (74 μg:28 μg), and cDNA was synthesized by using SuPrimeScript® RT premix 2× (GeNetBio).

Real-time PCR for confirming mRNA expression of DPP4 was performed by utilizing SYBR green 2× premix (Applied Biosystems) and AB StepOnePlus® real-time PCR system (Applied Biosystems—Thermo Fisher Scientific). Herein, the base sequence of a primer used for detection is as follows.

```
DPP4 sense:
                            (SEQ ID NO: 28)
TCCCAACTCCAGAGGACAAC DPP4 antisense:
                            (SEQ ID NO: 29)
CAGGGCTTTGGAGATCTGAG GAPDH sense:
                            (SEQ ID NO: 30)
GCACCGTCAAGGCTGAGAA GAPDH antisense:
                            (SEQ ID NO: 31)
AGGGATCTCGCTCCTGGAA
```

Moreover, cells were collected after treatment of human liver cancer cells (SNU398) with each nano-liposome produced in the present invention under the same conditions as an mRNA expression confirmation experiment, and the proteins from the cells were extracted by treating the cells with RIPA buffer (Sigma). Also, a DPP4 protein expression level was detected through anti-DPP4 (mouse) (Origene, TA500733) and anti-GAPDH (mouse) (Santa Cruz Biotechnology, Inc., Dallas Tex., sc-32233).

Figure 8A:
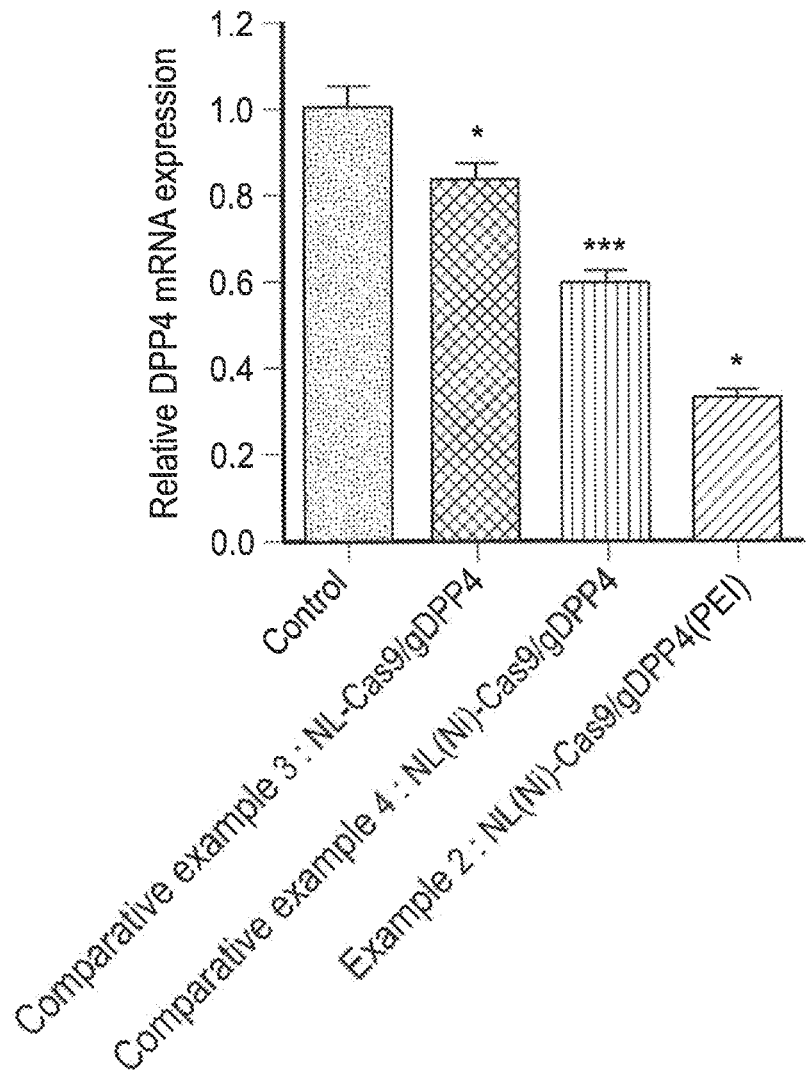
FIGS. 8A-8C are a series of graphs that show the results of a WST-1 assay showing the changes observed in the expression of DPP4, which is a target gene, by treating human liver cancer cells with a nano-liposome of the present invention (FIG. 8A—mRNA expression of DPP4.
Figure 8B:
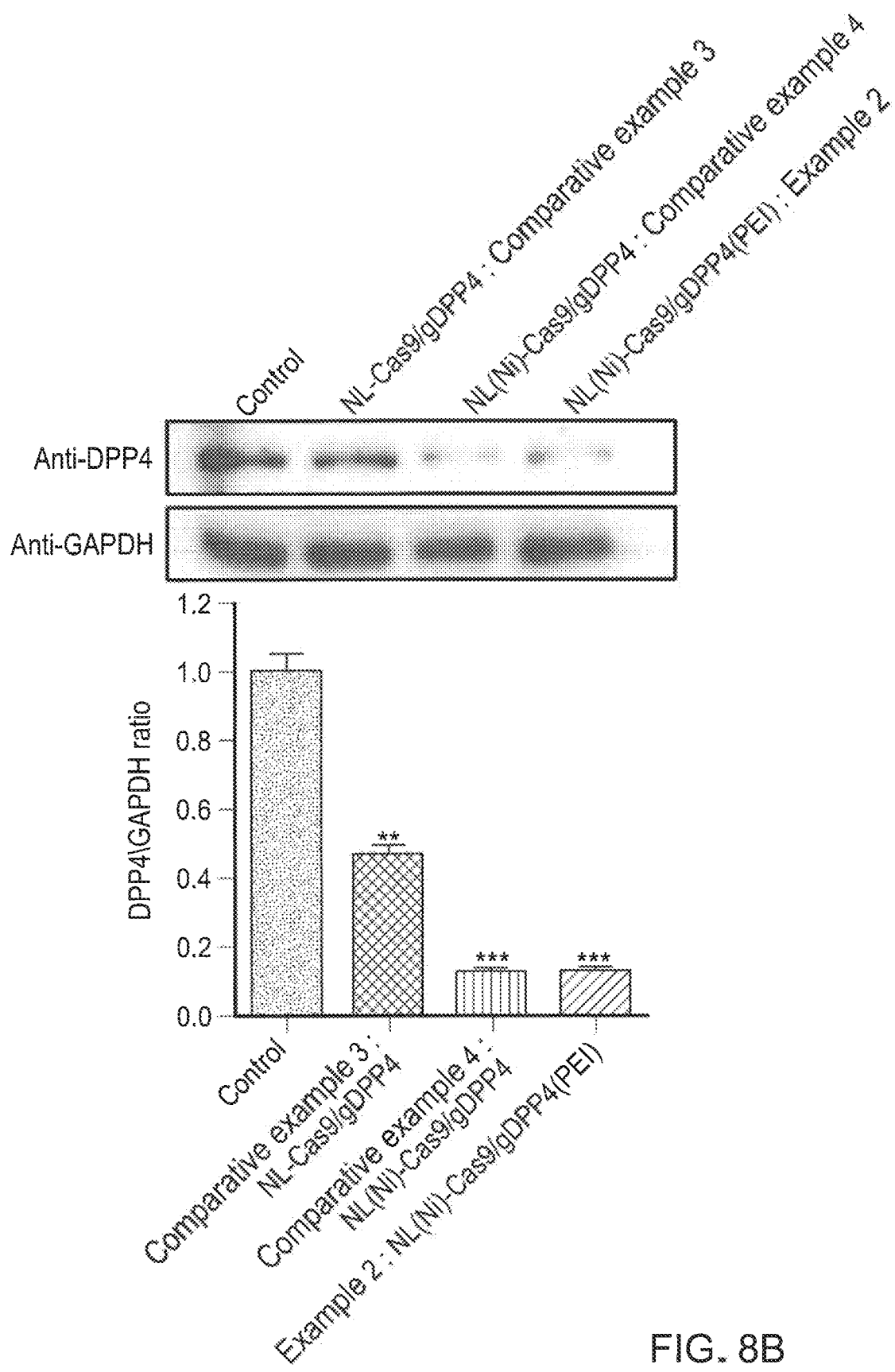
Figure 8C:
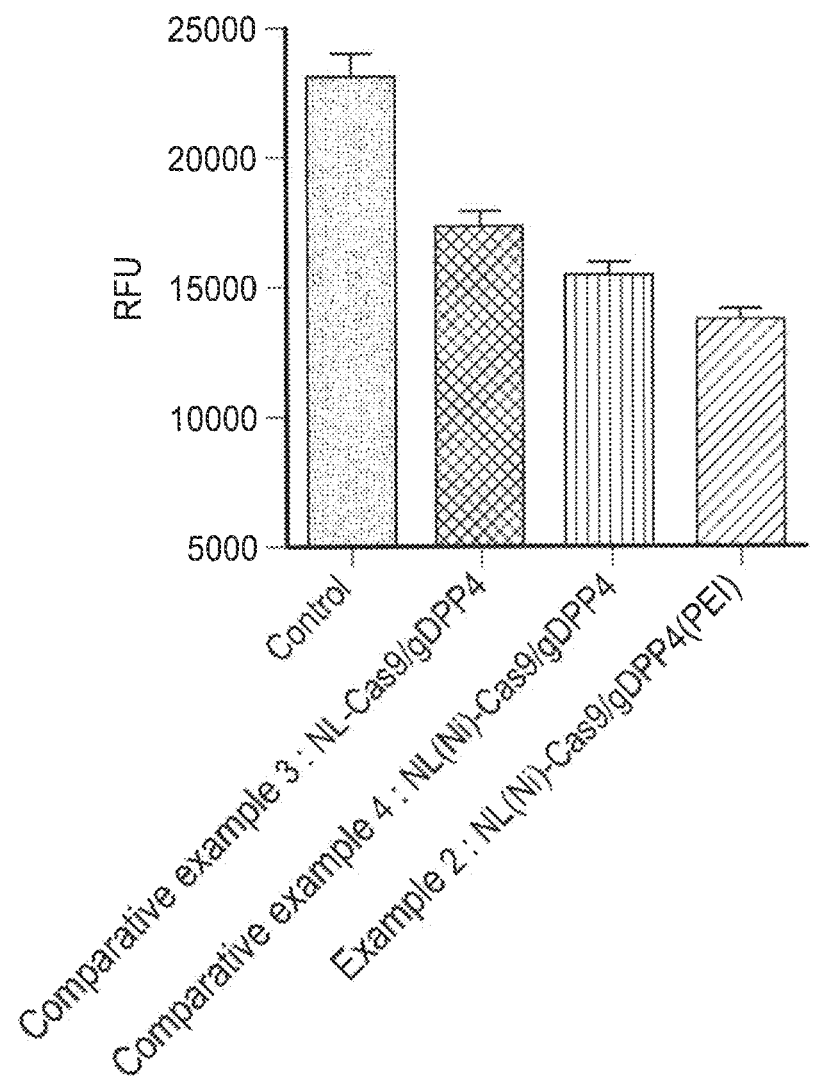

According to the results of the experiment, there was little variation between the different kinds of guide RNA strands, and a representative result is shown in FIGS. 8A-8C, wherein the guide RNA of SEQ ID NO: 2 was included. FIGS. 8A and 8B (FIG. 8B top part is an image of a protein electrophoresis gel, and FIG. 8B bottom part is a quantified bar graph thereof) confirm that the nano-liposome of Example 2 effectively limits mRNA and protein expression of DPP4.

Experimental Example 2-4—DPP4 Activity Measurement

With respect to the activity of DPP4, a DPP4 assay kit (Abnova) was used as the default material. After treating with each nano-liposome (human target) produced in the present invention, a substrate solution (H-Gly-Pro-AMC) was added to a cell (SNU398)-extracted protein and reacted at 37° C. for 30 minutes. After the reaction, a sodium acetate solution (1M, pH 5.0) is added to stop the reaction. DPP4 activity was measured by measuring the fluorescence value using an excitation wavelength of 360 nm and an emission wavelength of 460 nm.

The result is shown in the bar graph of FIG. 8C, and it can be seen that the nano-liposome of Example 2 most effectively limits expression of a DPP4 gene.

Experimental Example 3—Confirmation of Cell Survival Rate and an Increasing Rate Cell survival rates and proliferation rates were confirmed using a WST-1 assay. To this end, an EZ-Cytox (DoGen, EZ-3000) kit was used, and a human liver cancer cell (SNU398) was cultured on a 96 well plate for 24 hours at a density of $5 \times 10^3$ for each well. Then, nano-liposomes (human target) produced in Example 2 and Comparative Example 1-4 and Cas9/gDPP4 (PEI) were applied to the human liver cancer cells and then removed by a culture liquid after 24 hours. Then, a WST-1 solution was treated to have a concentration of 10% (v/v). *Cas9/gDPP4(PEI): a composite of Cas9 protein/guide RNA/polyethyleneimine was applied without being encapsulated in a nano-liposome.

Absorbance at 460 nm was measured after 2 hours, and cell survival and proliferation were compared with those of a control group (non-treatment group). Cytotoxicity evaluation was performed at 24 hour intervals for 72 hours following treatment. According to the results, there was little variation between the different kinds of guide RNA strands, and a representative result is shown in the bar graph of FIG. 9, wherein the guide RNA of SEQ ID NO: 2 was used.

Figure 9:
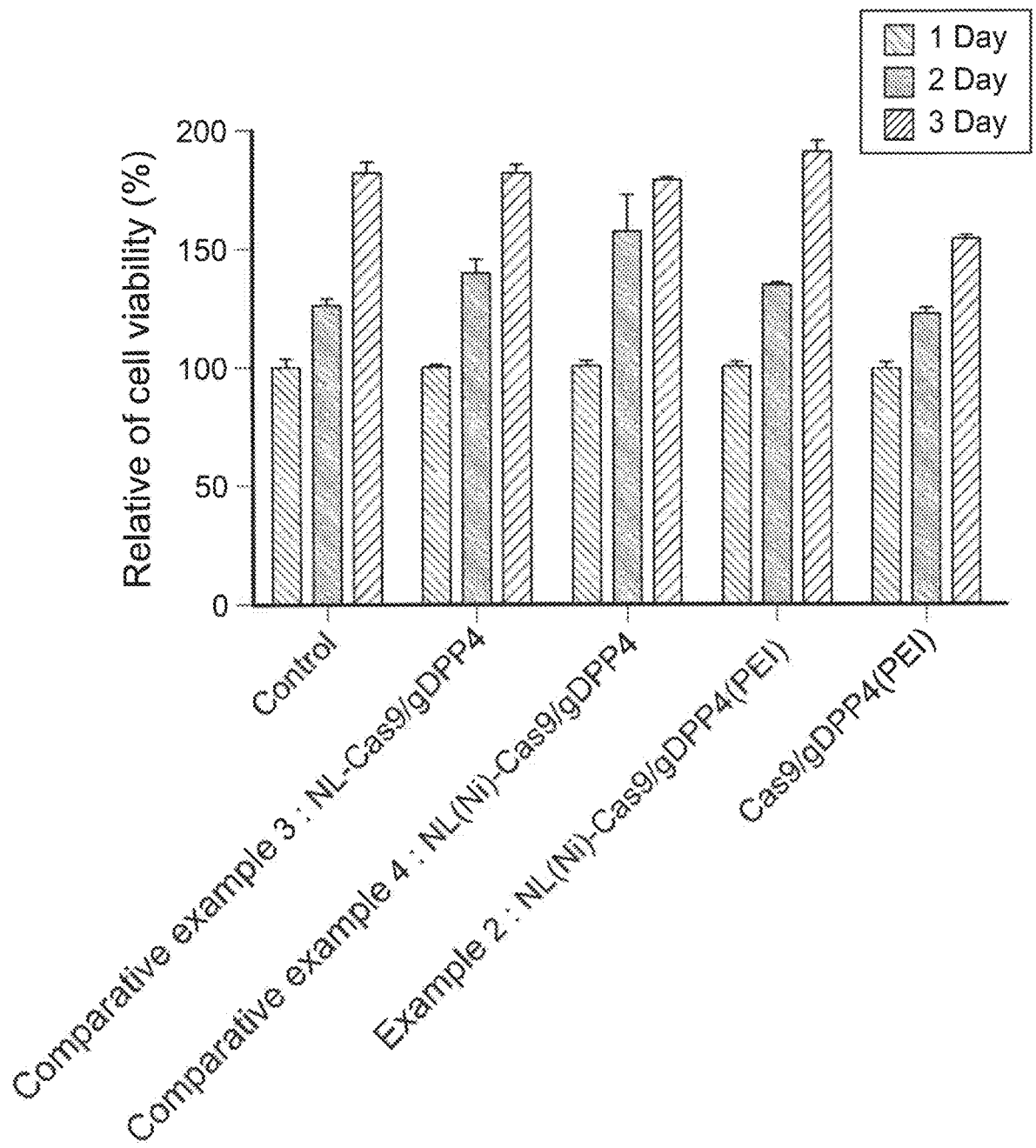
FIG. 9 is a graph that shows the results of a WST-1 assay showing the survival/proliferation of cells when a nano-liposome produced as described herein is used to treat human liver cancer cells.

FIG. 9 confirms that cell proliferation and survival of a sample treated by nano-liposomes produced in Example 2 and Comparative Examples 1-4 do not show a significant change compared to a non-treating group. This experiment demonstrate that the nano-liposomes of the present invention have excellent biocompatibility and are not harmful to the proliferation and the growth of cells.

Experimental Example 4—Confirmation of Inhibition of DPP4 Expression in a Type-2 Diabetes Animal Model An in vive application experiment was performed through comparison with a DPP4 inhibitor (sitagliptin) that is currently in use. The nano-liposome (200 μl, solvent PBS) (animal target) of Example 2 was administered once through intravenous injection into db/db mice at a concentration at which Cas9:gRNA is 1.48 μg:0.56 μg. The nano-liposomes used in this experiment included both SEQ ID NO: 7 and SEQ ID NO: 8.

Figure 10:
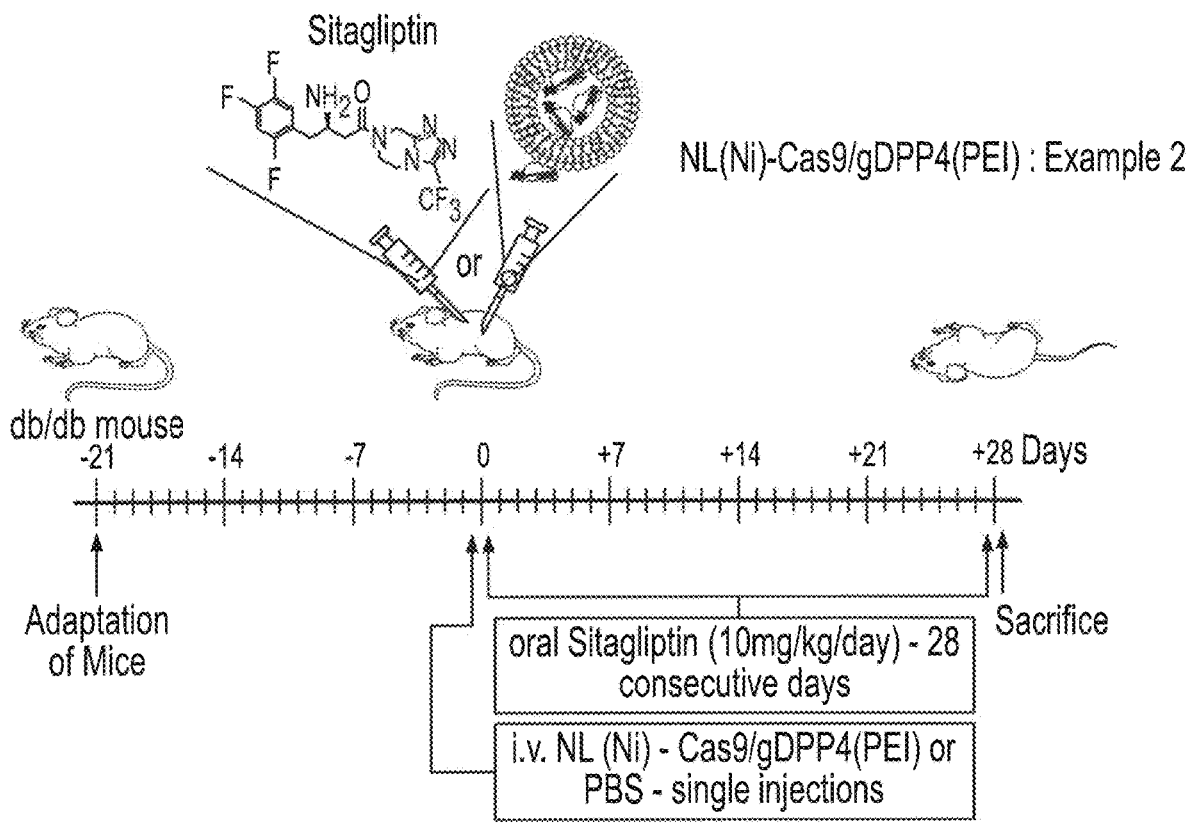
FIG. 10 is a schematic that illustrates a timetable in which a nano-liposome produced in Example 2 as described herein is applied to a type 2 diabetes animal model.
Figure 11A:
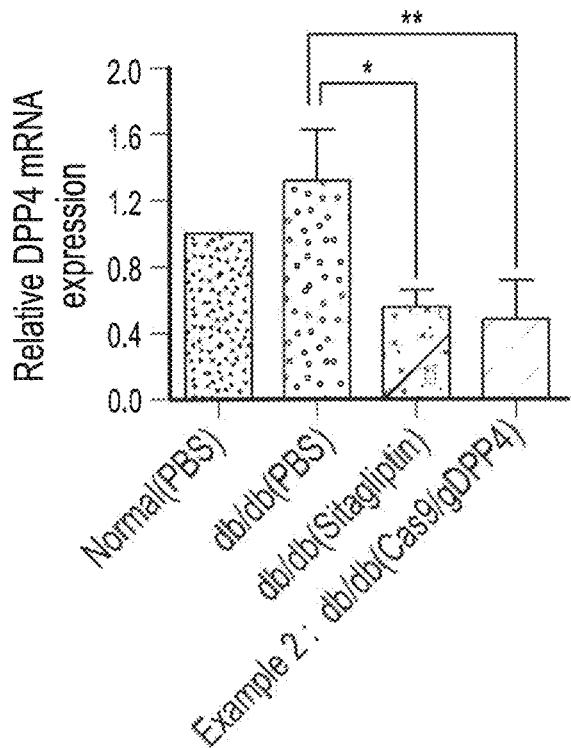
FIGS. 11A-11C are a series of graphs (11A and 11C) and a gel (11B) that show the results of observing the change in expression of mRNA and protein of a target gene (DPP4) in liver tissue by applying a nano-liposome produced in Example 2 as described herein to a type 2 diabetes animal model.
Figure 11B:
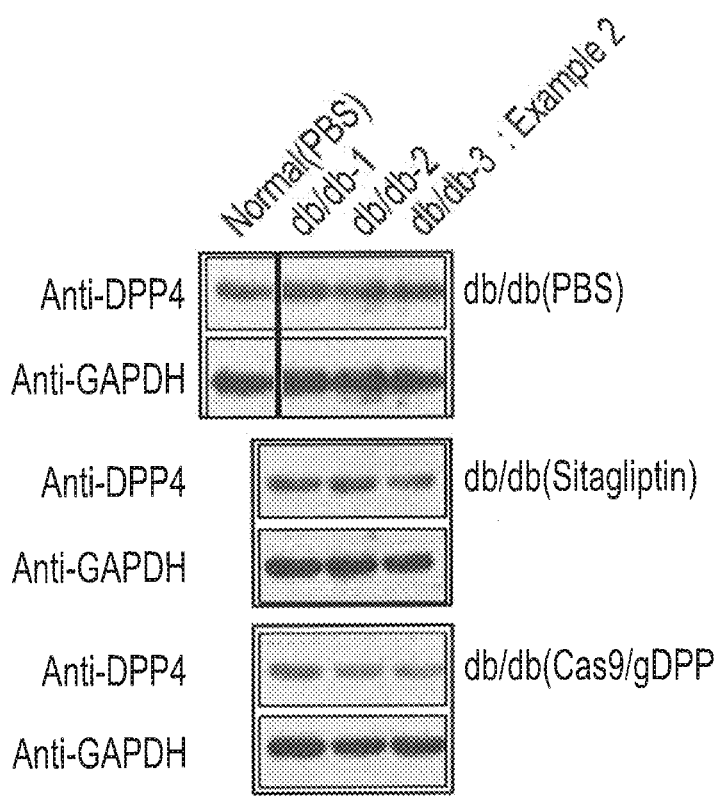
Figure 11C:
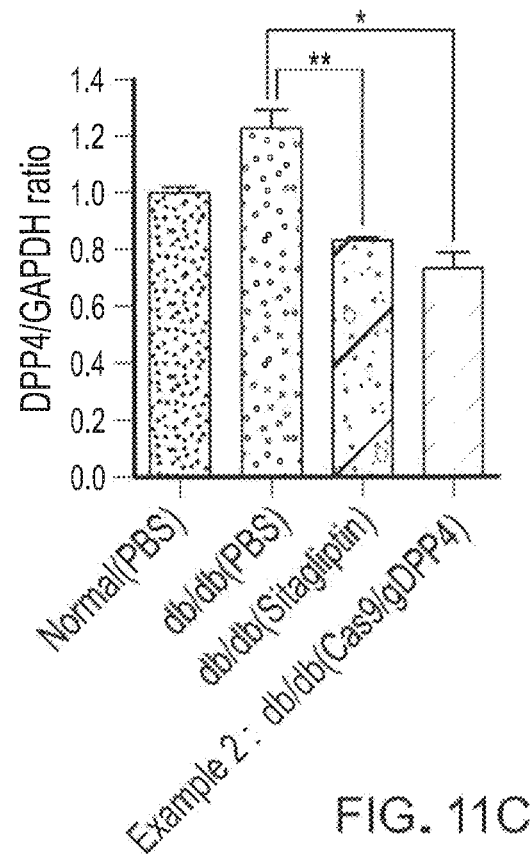

A DPP4 inhibitor was orally administered at a concentration of 10 mg/day every day until the experiment was finished, and PBS was administered to the control group of a disease model mice and to normal mice (non-disease model-C57BL/6) (designated "db/db(PBS)" and "Normal (PBS)") (a group of mice in which sitagliptin was administered was designated "db/db(sitagliptin)"). The in vive experiment time line is shown in FIG. 10. Weight and blood sugar of the test animals were checked every 3 days during the in vive experiment.

After the experiment was finished, an organ (liver, pancreas) of the test animal was extracted. Changes in the expression of a target gene were confirmed through immunostaining.

Here, the expression level of mRNA and protein of DPP4 were measured using the same method as a cell experiment, and primers used for analyzing mRNA consists of the base sequences below:

```
DPP4 sense:
                                    (SEQ ID NO: 28)
TCCCAACTCCAGAGGACAAC DPP4 antisense:
                                    (SEQ ID NO: 29)
CAGGGCTTTGGAGATCTGAG GAPDH sense:
                                    (SEQ ID NO: 30)
GCACCGTCAAGGCTGAGAA GAPDH antisense:
                                    (SEQ ID NO: 31)
AGGGATCTCGCTCCTGGAA
```

To perform immunostaining, animal tissues were extracted and then fixed to 4% paraformaldehyde, and then tissue molds were produced by using a paraffin mold method. Next, a tissue slide was obtained by slicing the tissue molds to 5 μm. Staining was performed using a DPP4 antibody and 3,3-diaminobenzidine tablets (DAB, sigma, D4418) on the slide.

Figure 12:
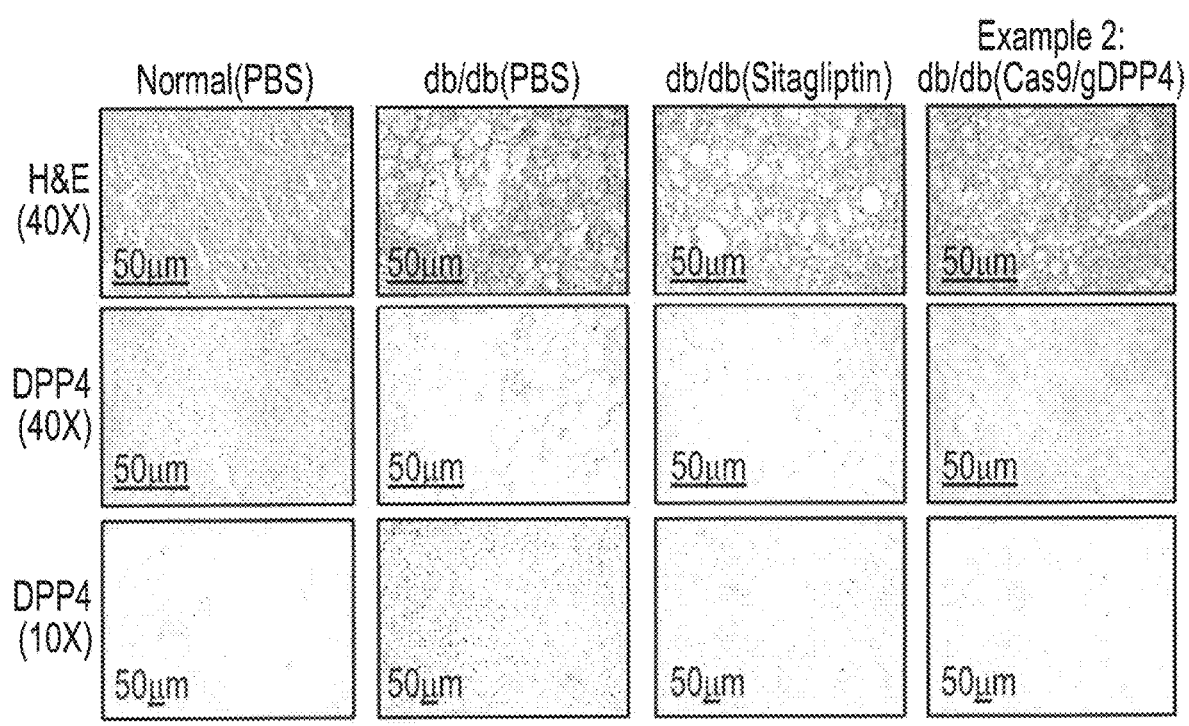
FIG. 12 is a series of microscope images that shows the results of observing the expression of a target gene (DPP4) in liver tissue through immunostaining after applying a nano-liposome produced in Example 2 as described herein to a type 2 diabetes animal model.
Figure 13A:
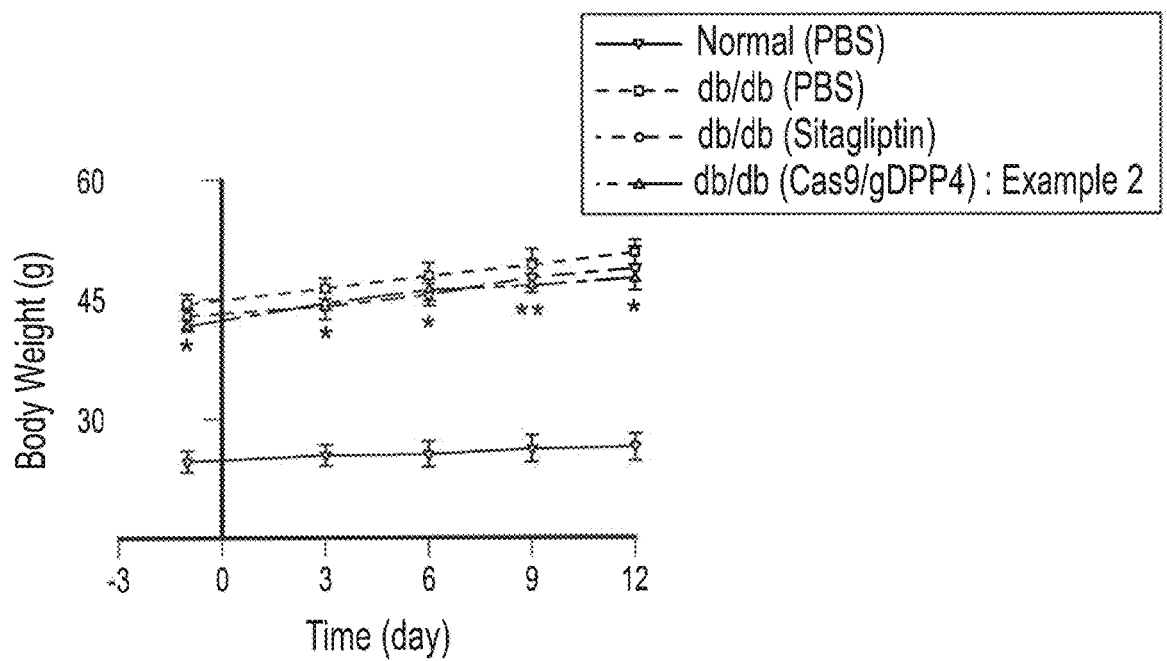
FIGS. 13A and 13B are a pair of graphs that show the change in the weight and blood sugar, respectively, of a test animal after applying a nano-liposome produced in Example 2 as described herein to a type 2 diabetes animal model.
Figure 13B:
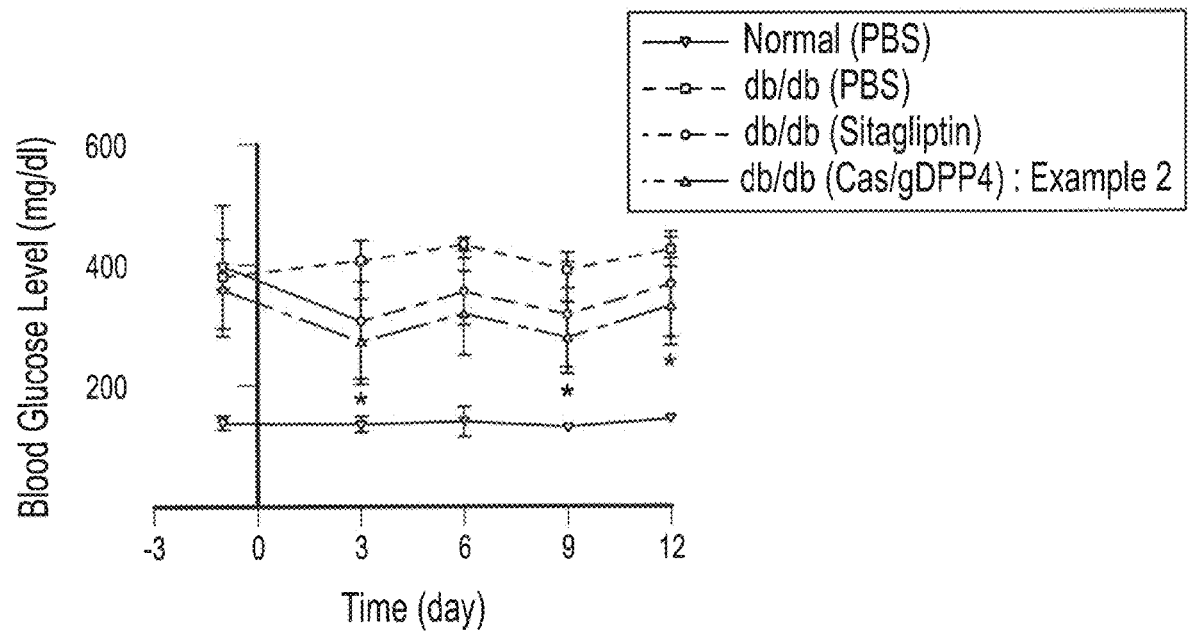
Figure 14:
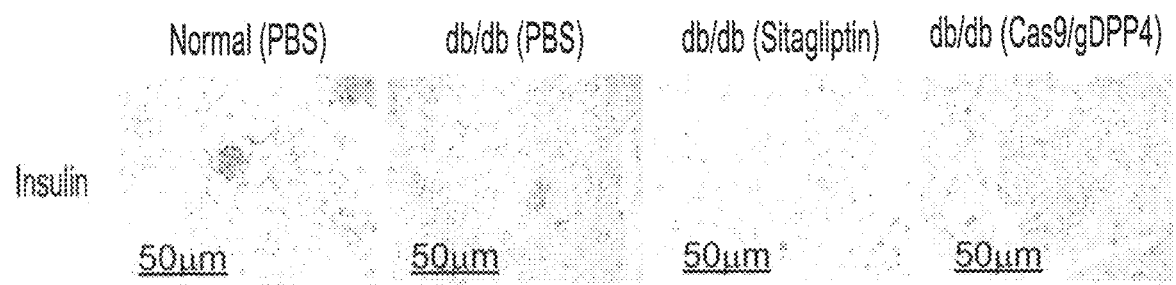
FIG. 14 is a series of microscope images that shows the results of observing the expression of insulin in a pancreas cell through immunostaining after applying a nano-liposome produced in Example 2 as described herein to a type 2 diabetes animal model.

Experimental results are shown in 11A-C, 12, 13A-B, and 14 and confirm that expression of DPP4, which is the target gene, is remarkably reduced in the liver tissue of the animal model to which the nano-liposome of Example 2 was administered, compared to a disease animal group to which a nano-liposome was not administered. In addition, the results show that a nano-liposome administration group has a blood sugar change, which is similar to a group to which a DPP4 inhibitor was administered every day. Also, the results of immunostaining shown in FIGS. 12 and 14 confirm that a region secreting insulin has increased in a similar manner to treatment with a DPP4 inhibitor. Meanwhile, the results confirm that each of the test results is similar even when a nano-liposome including only SEQ ID NO: 7 or SEQ ID NO: 8 is used.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:
   (a) a nano-liposome carrier comprising a metal chelating lipid; and
   (b) a hybrid Clustered Regularly Interspaced Short Palindromic Repeats (CRISPR) complex comprising:
      (i) a CRISPR-associated protein 9 (Cas9) protein,
      (ii) a guide RNA, and
      (iii) a cationic polymer;
   wherein the nano-liposome carrier encapsulates the hybrid CRISPR complex.

2. The composition of claim 1, wherein the guide RNA is a guide RNA that specifically binds to a target DNA of a human dipeptidyl peptidase-4 (DPP4).

3. The composition of claim 2, wherein the guide RNA comprises nucleic acid sequence UUUGGGC-CAUUUGGGGAGUU (SEQ ID NO:1) and the target DNA comprises nucleic acid sequence AACTCCC-CAAATGGCCCAAA (SEQ ID NO:5).

4. The composition of claim 1, wherein the nano-liposome carrier further comprises lecithin or cholesterol, or both lecithin and cholesterol.

5. The composition of claim 3, wherein the lecithin comprises α-phosphatidylcholine.

6. The composition of claim 1, wherein the metal chelating lipid is selected from the group consisting of:
   1,2-dioleoyl-sn-glycero-3-[(N-5-amino-1-carboxypentyl) iminodiacetic acid) succinyl] (nickel salt) ("DOGS-NTA-Ni");
   1,2-dimyristoyl-sn-glycero-3-phosphoethanolamine-N-diethylenetriamine-pentaacetic acid (gadolinium salt) ("DMPE-DTPA-Gd"); and
   1,2-dimyristoyl-sn-glycero-3-phosphoethanolamine-N-diethylenetriamine-pentaacetic acid (copper salt) ("DMPE-DTPA-Cu"),
   wherein the DOGS-NTA-Ni lipid has a chemical structure shown in Chemical Formula 1 below, Chemical Formula 1

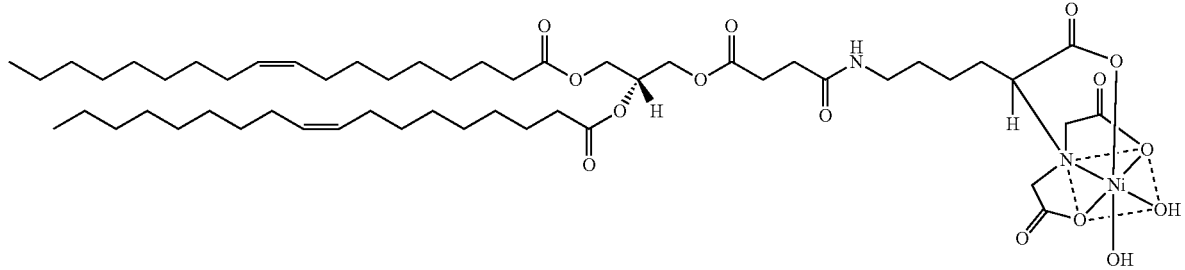

wherein the DMPE-DTPA-Gd lipid has a chemical structure shown in Chemical Formula 2 below, nano-liposome carrier at a molar ratio of 1.5-2.5:0.5-1.5:0.1-0.5.

Chemical Formula 2

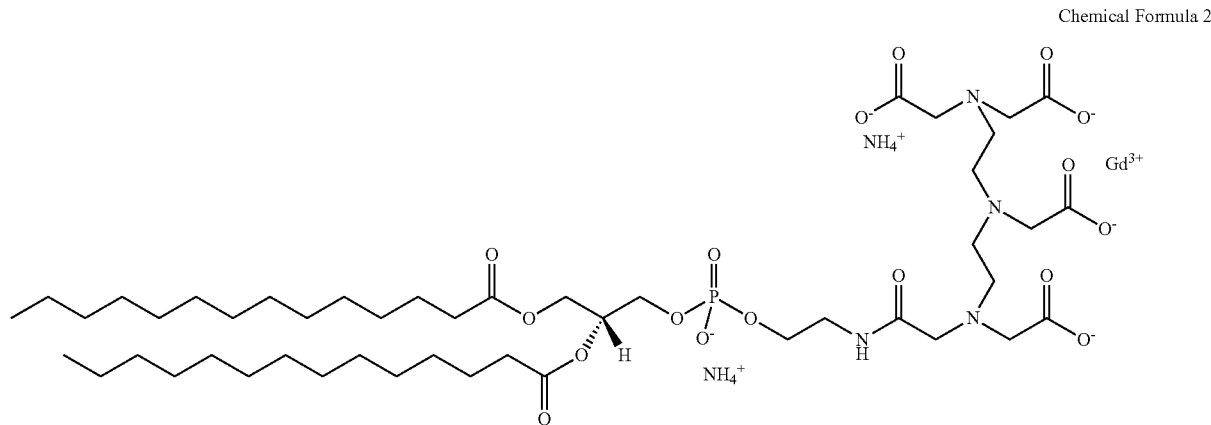

and,
wherein the DMPE-DTPA-Cu lipid has a chemical structure shown in Chemical Formula 3 below, Chemical Formula 3

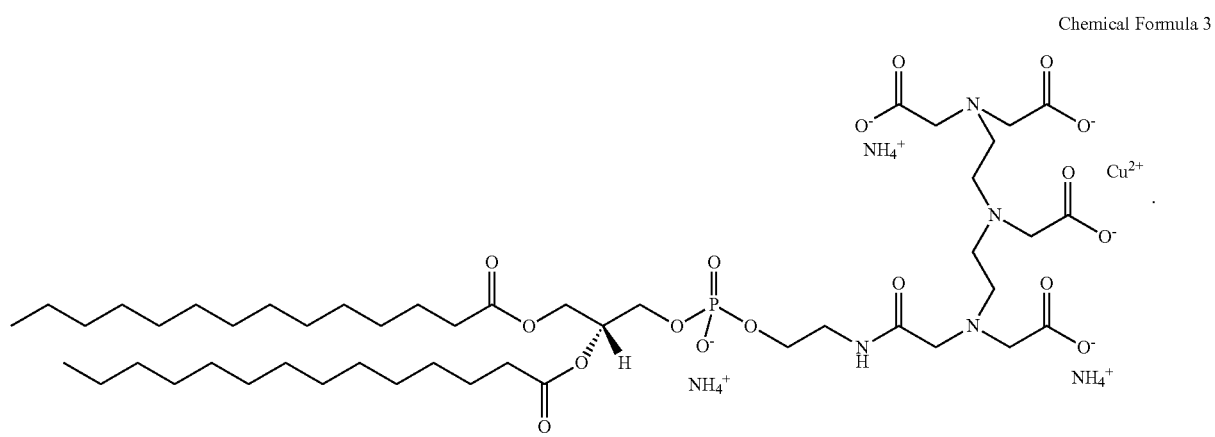

14. The composition of claim 13, wherein the guide RNA comprises nucleic acid sequence UUUGGGCAUUUGGGGAGUU (SEQ ID NO:1) or nucleic acid sequence GUCCGGUUUCGCCAGCUUUU (SEQ ID NO:2) and the target DNA comprises nucleic acid sequence AACTCCCCAAATGGCCCAAA (SEQ ID NO:5) or nucleic acid sequence AAAAGCTGGCGAAACCGGAC (SEQ ID NO:6).

15. The composition of claim 1, wherein the lecithin comprises α-phosphatidylcholine, the cationic polymer comprises polyethyleneimine (PEI), and the metal chelating lipid comprises DOGS-NTA-Ni.

16. The composition of claim 15, wherein the Cas9 protein, the guide RNA, and polyethyleneimine are present in the CRISPR complex at a molar ratio of 1:2:50, and the lecithin, DOGS-NTA-Ni lipid, and cholesterol are present in the nano-liposome carrier at a molar ratio of 2:1:0.3.

17. A method comprising administering to a subject an amount of a composition effective to reduce expression of a target gene, wherein the composition comprises:
(a) a nano-liposome carrier comprising metal chelating lipid; and
(b) a hybrid Clustered Regularly Interspaced Short Palindromic Repeats (CRISPR) complex comprising
(i) a CRISPR-associated protein 9 (Cas9) protein,
(ii) a guide RNA that specifically binds to a target gene, and
(iii) a cationic polymer;

7. The composition of claim 1, wherein the cationic polymer is selected from the group consisting of poly-L-lysine, polyamidoamine, poly[2-(N,N-dimethylamino)ethyl methacrylate], chitosan, poly-L-ornithine, cyclodextrin, histone, collagen, dextran, and polyethyleneimine (PEI).

8. The composition of claim 1, wherein the cationic polymer comprises polyethyleneimine (PEI).

9. The composition of claim 1, wherein the guide RNA comprises nucleic acid sequence GUCCGGUUUCGCCAGCUUUU (SEQ ID NO:2) and the target DNA comprises nucleic acid sequence AAAAGCTGGCGAAACCGGAC (SEQ ID NO:6).

10. The composition of claim 1, wherein the nano-liposome carrier has a diameter of 10 to 2,000 nm.

11. The composition of claim 1, wherein Cas9 protein and guide RNA are present in the CRISPR complex at a molar ratio of 1:1-3.

12. The composition of claim 11, wherein the Cas9 protein and the guide RNA are present in the CRISPR complex at a molar ratio of 1:1-3 and wherein the lecithin, the metal chelating lipid, and the cholesterol are present in the nano-liposome carrier at a molar ratio of 1.5-2.5:0.5-1.5:0.1-0.5.

13. The composition of claim 1, wherein the lecithin, metal chelating lipid, and cholesterol are present in the wherein the nano-liposome carrier encapsulates the hybrid CRISPR complex.

18. The method of claim 17, wherein the guide RNA is a guide RNA that specifically binds to a target DNA of a human dipeptidyl peptidase-4 (DPP4).

19. The method of claim 17, wherein the nano-liposome carrier further comprises lecithin or cholesterol, or both lecithin and cholesterol.

20. The method of claim 17, wherein the metal chelating lipid is selected from the group consisting of:
   1,2-dioleoyl-sn-glycero-3-[(N-5-amino-1-carboxypentyl) iminodiacetic acid) succinyl] (nickel salt) ("DOGS-NTA-Ni");
   1,2-dimyristoyl-sn-glycero-3-phosphoethanolamine-N-diethylenetriamine-pentaacetic acid (gadolinium salt) ("DMPE-DTPA-Gd"); and
   1,2-dimyristoyl-sn-glycero-3-phosphoethanolamine-N-diethylenetriamine-pentaacetic acid (copper salt) ("DMPE-DTPA-Cu"),
   wherein the DOGS-NTA-Ni lipid has a chemical structure shown in Chemical Formula 1 below, Chemical Formula 1

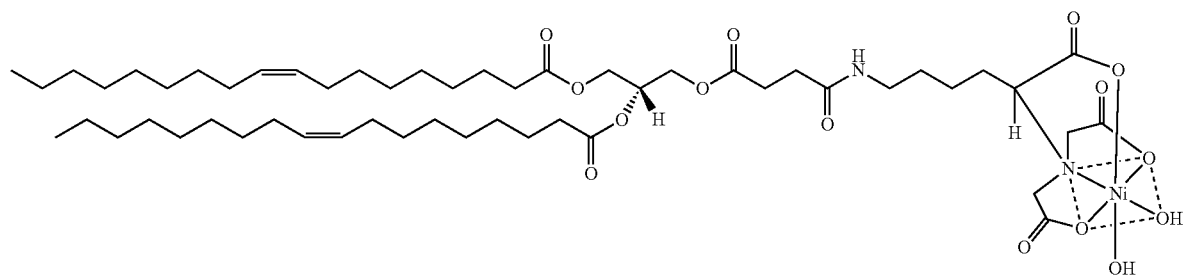

wherein the DMPE-DTPA-Gd lipid has a chemical structure shown in Chemical Formula 2 below, Chemical Formula 2

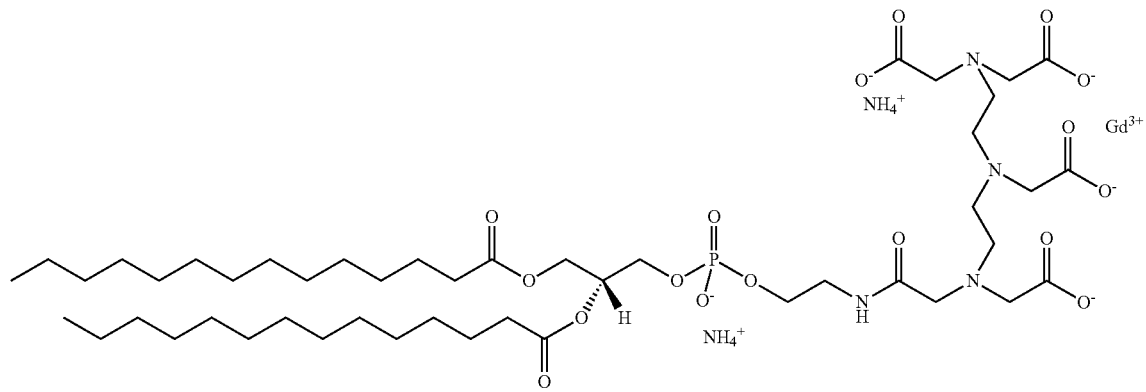

and,
   wherein the DMPE-DTPA-Cu lipid has a chemical structure shown in Chemical Formula 3 below,

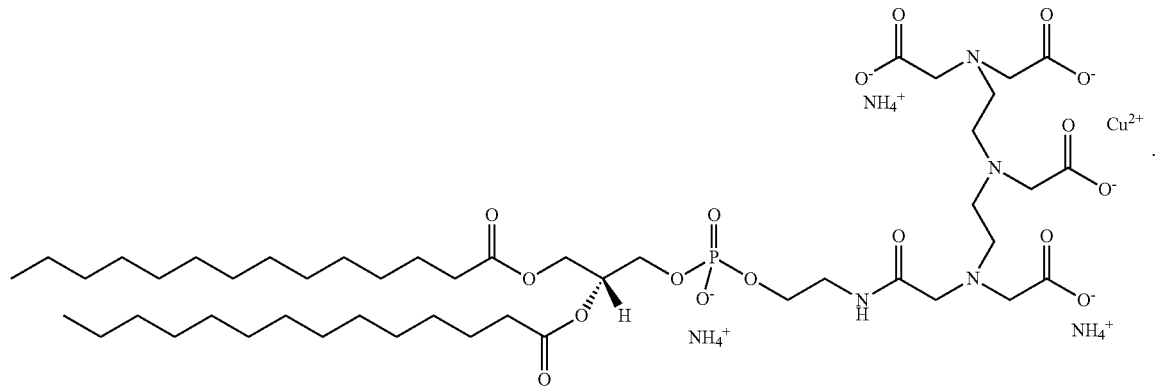

Chemical Formula 3

21. The method of claim 17, wherein the cationic polymer is selected from the group consisting of poly-L-lysine, polyamidoamine, poly[2-(N,N-dimethylamino)ethyl methacrylate], chitosan, poly-L-ornithine, cyclodextrin, histone, collagen, dextran, and polyethyleneimine (PEI).

22. The method of claim 17, wherein the guide RNA comprises nucleic acid sequence UUUGGGC-CAUUUGGGGAGUU (SEQ ID NO:1) or nucleic acid sequence GUCCGGUUUCGCCAGCUUUU (SEQ ID NO:2) and the target DNA comprises nucleic acid sequence AACTCCCCAAATGGCCCAAA (SEQ ID NO:5) or nucleic acid sequence AAAAGCTGGCGAAACCGGAC (SEQ ID NO:6).

\* \* \* \* \*

SEQUENCE LISTING

```
<160> NUMBER OF SEQ ID NOS: 31

<210> SEQ ID NO 1
<211> LENGTH: 20
<212> TYPE: RNA
<213> ORGANISM: Homo sapiens
```

<400> SEQUENCE: 1
uuugggccau uuggggaguu                                          20

<210> SEQ ID NO 2
<211> LENGTH: 20
<212> TYPE: RNA
<213> ORGANISM: Homo sapiens

<400> SEQUENCE: 2
guccgguuuc gccagcuuuu                                          20

<210> SEQ ID NO 3
<211> LENGTH: 20
<212> TYPE: DNA
<213> ORGANISM: Homo sapiens

<400> SEQUENCE: 3
tttgggccat ttggggagtt                                          20

<210> SEQ ID NO 4
<211> LENGTH: 20
<212> TYPE: DNA
<213> ORGANISM: Homo sapiens

<400> SEQUENCE: 4
gtccggtttc gccagctttt                                          20

<210> SEQ ID NO 5
<211> LENGTH: 20
<212> TYPE: DNA
<213> ORGANISM: Homo sapiens

<400> SEQUENCE: 5
aactccccaa atggcccaaa                                          20

<210> SEQ ID NO 6
<211> LENGTH: 20
<212> TYPE: DNA
<213> ORGANISM: Homo sapiens

<400> SEQUENCE: 6
aaaagctggc gaaaccggac                                          20

<210> SEQ ID NO 7
<211> LENGTH: 20
<212> TYPE: RNA
<213> ORGANISM: Mus musculus

<400> SEQUENCE: 7
ucaaguccua cucuuugugg                                          20

<210> SEQ ID NO 8
<211> LENGTH: 20
<212> TYPE: RNA
<213> ORGANISM: Mus musculus

<400> SEQUENCE: 8
ccaauaguuc ugcugagcaa                                          20

<210> SEQ ID NO 9
<211> LENGTH: 20
<212> TYPE: DNA
<213> ORGANISM: Mus musculus

```
<400> SEQUENCE: 9
tcaagtccta ctctttgtgg                                                  20

<210> SEQ ID NO 10
<211> LENGTH: 20
<212> TYPE: DNA
<213> ORGANISM: Mus musculus

<400> SEQUENCE: 10
ccaatagttc tgctgagcaa                                                  20

<210> SEQ ID NO 11
<211> LENGTH: 20
<212> TYPE: DNA
<213> ORGANISM: Mus musculus

<400> SEQUENCE: 11
ccacaaagag taggacttga                                                  20

<210> SEQ ID NO 12
<211> LENGTH: 20
<212> TYPE: DNA
<213> ORGANISM: Mus musculus

<400> SEQUENCE: 12
ttgctcagca gaactattgg                                                  20

<210> SEQ ID NO 13
<211> LENGTH: 104
<212> TYPE: RNA
<213> ORGANISM: Homo sapiens

<400> SEQUENCE: 13
uuugggccau uugggagguu guuuuagagc uagaaauagc aaguuaaaau aaggcuaguc      60
cguuaucaac uugaaaaagu ggcaccgagu cggugcuuuu uuuu                      104

<210> SEQ ID NO 14
<211> LENGTH: 104
<212> TYPE: RNA
<213> ORGANISM: Homo sapiens

<400> SEQUENCE: 14
guccgguuuc gccagcuuuu guuuuagagc uagaaauagc aaguuaaaau aaggcuaguc      60
cguuaucaac uugaaaaagu ggcaccgagu cggugcuuuu uuuu                      104

<210> SEQ ID NO 15
<211> LENGTH: 104
<212> TYPE: RNA
<213> ORGANISM: Mus musculus

<400> SEQUENCE: 15
ucaaguccua cucuuugugg guuuuagagc uagaaauagc aaguuaaaau aaggcuaguc      60
cguuaucaac uugaaaaagu ggcaccgagu cggugcuuuu uuuu                      104

<210> SEQ ID NO 16
<211> LENGTH: 104
<212> TYPE: RNA
<213> ORGANISM: Mus musculus

<400> SEQUENCE: 16
```
ccaauaguuc ugcugagcaa guuuuagagc uagaaauagc aaguuaaaau aaggcuaguc      60
cguuaucaac uugaaaaagu ggcaccgagu cggugcuuuu uuuu                     104

<210> SEQ ID NO 17
<211> LENGTH: 104
<212> TYPE: RNA
<213> ORGANISM: Homo sapiens

<400> SEQUENCE: 17
uuugggccau uuggggaguu guuuuagagc uagaaauagc aaguuaaaau aaggcuaguc      60
cguuaucaac uugaaaaagu ggcaccgagu cggugcuuuu uuuu                     104

<210> SEQ ID NO 18
<211> LENGTH: 104
<212> TYPE: RNA
<213> ORGANISM: Homo sapiens

<400> SEQUENCE: 18
guccgguuuc gccagcuuuu guuuuagagc uagaaauagc aaguuaaaau aaggcuaguc      60
cguuaucaac uugaaaaagu ggcaccgagu cggugcuuuu uuuu                     104

<210> SEQ ID NO 19
<211> LENGTH: 104
<212> TYPE: RNA
<213> ORGANISM: Mus musculus

<400> SEQUENCE: 19
ucaaguccua cucuuugugg guuuuagagc uagaaauagc aaguuaaaau aaggcuaguc      60
cguuaucaac uugaaaaagu ggcaccgagu cggugcuuuu uuuu                     104

<210> SEQ ID NO 20
<211> LENGTH: 104
<212> TYPE: RNA
<213> ORGANISM: Mus musculus

<400> SEQUENCE: 20
ccaauaguuc ugcugagcaa guuuuagagc uagaaauagc aaguuaaaau aaggcuaguc      60
cguuaucaac uugaaaaagu ggcaccgagu cggugcuuuu uuuu                     104

<210> SEQ ID NO 21
<211> LENGTH: 21
<212> TYPE: DNA
<213> ORGANISM: Artificial Sequence
<220> FEATURE:
<223> OTHER INFORMATION: synthetic primer

<400> SEQUENCE: 21
gttttagagc tagaaatagc a                                               21

<210> SEQ ID NO 22
<211> LENGTH: 21
<212> TYPE: DNA
<213> ORGANISM: Artificial Sequence
<220> FEATURE:
<223> OTHER INFORMATION: synthetic primer

<400> SEQUENCE: 22
aaaagcaccg actcggtgcc a                                               21

<210> SEQ ID NO 23
<211> LENGTH: 21

```
<212> TYPE: DNA
<213> ORGANISM: Artificial Sequence
<220> FEATURE:
<223> OTHER INFORMATION: synthetic primer

<400> SEQUENCE: 23
gtgagtgccg cgccacgtac g                                            21

<210> SEQ ID NO 24
<211> LENGTH: 21
<212> TYPE: DNA
<213> ORGANISM: Artificial Sequence
<220> FEATURE:
<223> OTHER INFORMATION: synthetic primer

<400> SEQUENCE: 24
ctgcaagccg agcagatcaa g                                            21

<210> SEQ ID NO 25
<211> LENGTH: 50
<212> TYPE: DNA
<213> ORGANISM: Homo sapiens

<400> SEQUENCE: 25
gagctctcgc ttagctttcg gaccctggct tctgctagga ccctggcgtc             50

<210> SEQ ID NO 26
<211> LENGTH: 32
<212> TYPE: DNA
<213> ORGANISM: Homo sapiens

<400> SEQUENCE: 26
gagctctcgc ttagctttcg gaccctggcg tc                                32

<210> SEQ ID NO 27
<211> LENGTH: 18
<212> TYPE: DNA
<213> ORGANISM: Homo sapiens

<400> SEQUENCE: 27
ggaccctggc ttctgcta                                                18

<210> SEQ ID NO 28
<211> LENGTH: 20
<212> TYPE: DNA
<213> ORGANISM: Artificial Sequence
<220> FEATURE:
<223> OTHER INFORMATION: synthetic primer

<400> SEQUENCE: 28
tcccaactcc agaggacaac                                              20

<210> SEQ ID NO 29
<211> LENGTH: 20
```

```
<212> TYPE: DNA
<213> ORGANISM: Artificial Sequence
<220> FEATURE:
<223> OTHER INFORMATION: synthetic primer

<400> SEQUENCE: 29
cagggctttg gagatctgag                                              20

<210> SEQ ID NO 30
<211> LENGTH: 19
<212> TYPE: DNA
<213> ORGANISM: Artificial Sequence
<220> FEATURE:
<223> OTHER INFORMATION: synthetic primer

<400> SEQUENCE: 30
gcaccgtcaa ggctgagaa                                               19

<210> SEQ ID NO 31
<211> LENGTH: 19
<212> TYPE: DNA
<213> ORGANISM: Artificial Sequence
<220> FEATURE:
<223> OTHER INFORMATION: synthetic primer

<400> SEQUENCE: 31
agggatctcg ctcctggaa                                               19
```